(12) United States Patent
Chakeres

(10) Patent No.: US 6,872,213 B2
(45) Date of Patent: Mar. 29, 2005

(54) STEREOTACTIC APPARATUS AND METHODS

(75) Inventor: Donald W. Chakeres, Upper Arlington, OH (US)

(73) Assignee: The Ohio State University, Columbus, OH (US)

(*) Notice: Subject to any disclaimer, the term of this patent is extended or adjusted under 35 U.S.C. 154(b) by 435 days.

(21) Appl. No.: 10/172,854

(22) Filed: Jun. 17, 2002

(65) Prior Publication Data

US 2002/0151783 A1 Oct. 17, 2002

Related U.S. Application Data

(62) Division of application No. 09/394,585, filed on Sep. 13, 1999, now Pat. No. 6,406,482.

(51) Int. Cl.[7] ............................................. A61B 19/00
(52) U.S. Cl. ...................................... 606/130; 600/429
(58) Field of Search .......................... 606/130; 600/417, 600/427, 409, 429; 604/116

(56) References Cited

U.S. PATENT DOCUMENTS

| | | | |
|---|---|---|---|
| 4,551,678 A | 11/1985 | Morgan et al. | 324/300 |
| 4,583,538 A | 4/1986 | Onik et al. | 128/303 |
| 4,618,978 A | 10/1986 | Cosman | 378/164 |
| 4,638,798 A | 1/1987 | Shelden et al. | 606/130 |
| 4,722,336 A | 2/1988 | Kim et al. | 128/303 |
| 4,750,487 A | 6/1988 | Zanetti | 606/130 |
| 5,030,223 A | 7/1991 | Anderson | 606/130 |
| 5,053,042 A | 10/1991 | Bidwell | 606/130 |
| 5,142,559 A | 8/1992 | Wielopolski et al. | 378/205 |
| 5,147,372 A | 9/1992 | Nymark et al. | 606/130 |
| 5,263,956 A | 11/1993 | Nobles | 606/130 |
| 5,309,913 A | 5/1994 | Kormos et al. | 600/429 |
| 5,383,454 A | 1/1995 | Bucholz | 600/429 |
| 5,426,685 A | 6/1995 | Pellegrino et al. | 378/87 |
| 5,437,280 A | 8/1995 | Hussman | 128/653.2 |
| 5,447,154 A | 9/1995 | Cinquin et al. | 128/653.1 |
| 5,499,989 A | 3/1996 | LaBash | 606/130 |
| 5,628,315 A | 5/1997 | Vilsmeier et al. | 128/653.1 |
| 5,678,549 A | 10/1997 | Heywang-Koebrunner et al. | 128/653.5 |
| 5,690,108 A | 11/1997 | Chakeres | 128/653.1 |
| 5,830,219 A | 11/1998 | Bird et al. | 606/130 |
| 5,913,863 A | 6/1999 | Fischer et al. | 606/130 |
| 5,971,998 A | 10/1999 | Russell et al. | 606/130 |
| 6,159,221 A | 12/2000 | Chakeres | 606/130 |
| 6,261,299 B1 | 7/2001 | Chakeres | 606/130 |
| 6,406,482 B1 | 6/2002 | Chakeres | 600/429 |
| 6,491,702 B2 * | 12/2002 | Heilbrun et al. | 606/130 |
| 6,678,545 B2 * | 1/2004 | Bucholz | 600/429 |

* cited by examiner

*Primary Examiner*—Kevin T. Truong
(74) *Attorney, Agent, or Firm*—Standley Law Group LLP

(57) ABSTRACT

The present invention includes stereotactic vectors, no electronic calculations and imaging, diagnostic and treatment techniques. The invention also includes machines or instruments using those aspects of the invention. The present invention also includes methods and processes using the devices of the present invention.

2 Claims, 24 Drawing Sheets

PATTERN VIEW FROM ABOVE
SHOWING MULTIPLE PARALLEL
DIFFERENT SECTION PLANES

COMPARISON OF V1 MINUS V2
VERSUS DEGREES
FOR VARIOUS
SECTION PLANES

REAL-SPACE VIEW OF PATTERN DESIGN

CT SCOUT VIEW OF PATTERN DESIGN

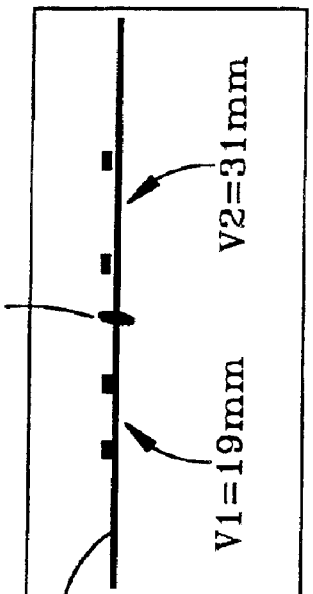
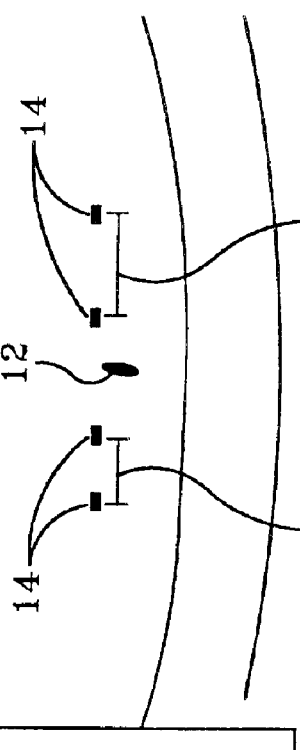
FIG-12

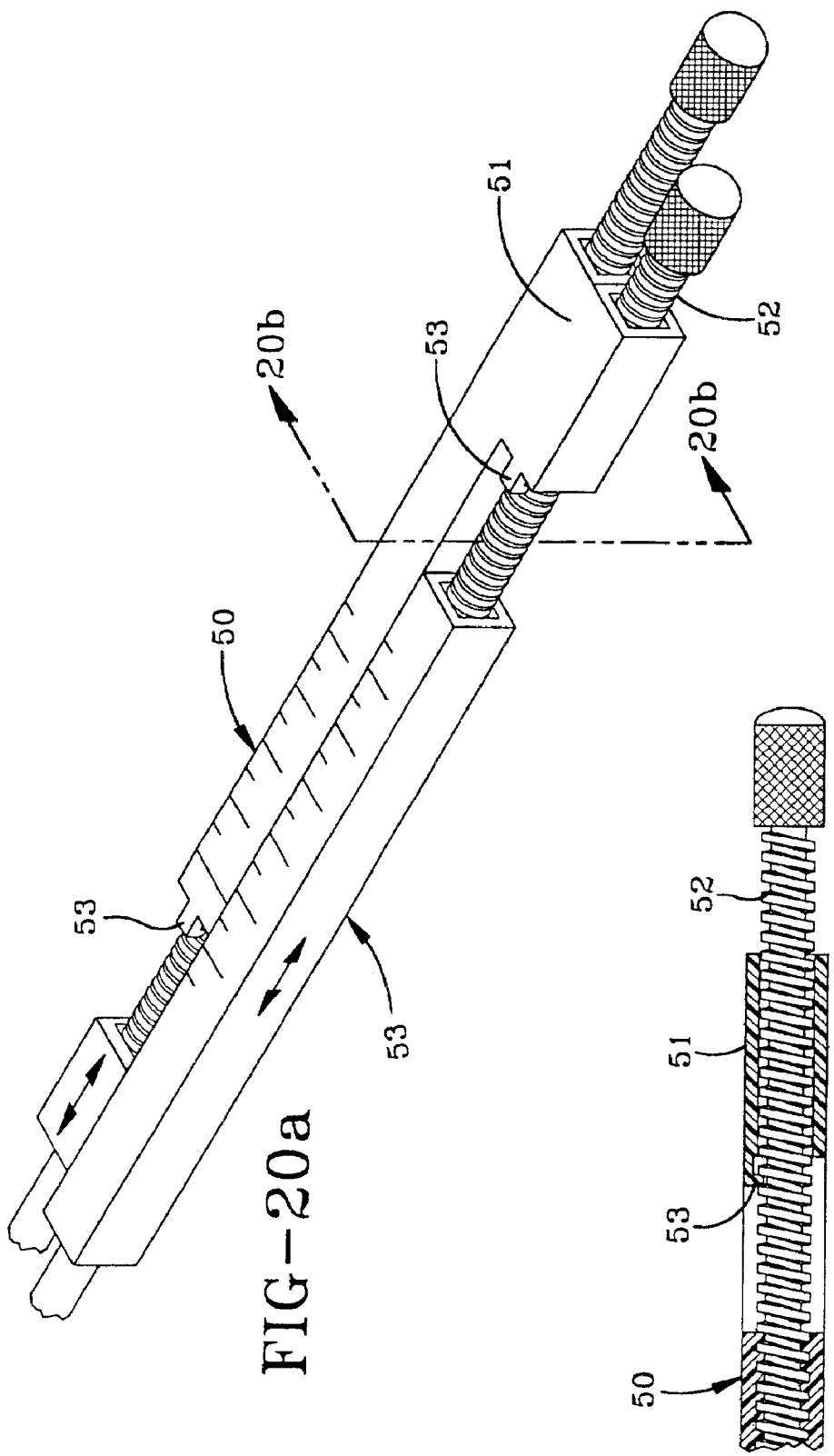

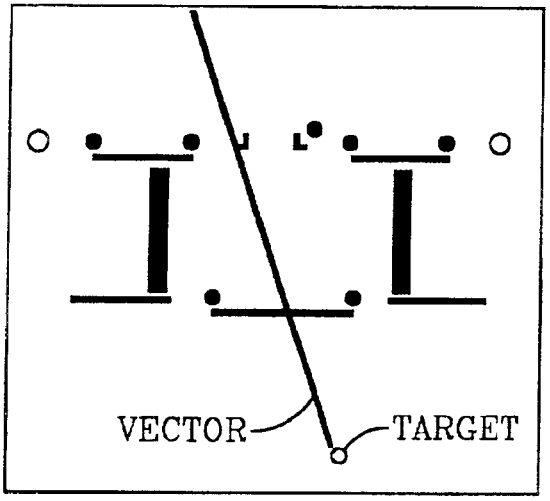

STEP 1:
MEASURE TOP V1 AND V2 mm, CONFIRM V1 AND V2 ARE THE SAME, IF NOT ROTATE DEVICE V1-V2 DEGREES ON CALIBRATED SCALE WITH REMOTE CONTROL HANDLE.

STEP 2:
DEFINE VECTOR TOWARDS TARGET WITH IMAGER LINE TOOL.

STEP 3:
MEASURE BOTTOM V DISTANCE (SLICE PLANE LOCATION) AND DISTANCE TO CLOSEST LIMB THAT THE VECTOR INTERSECTS (SKIN ENTRY POINT)

FIG-25

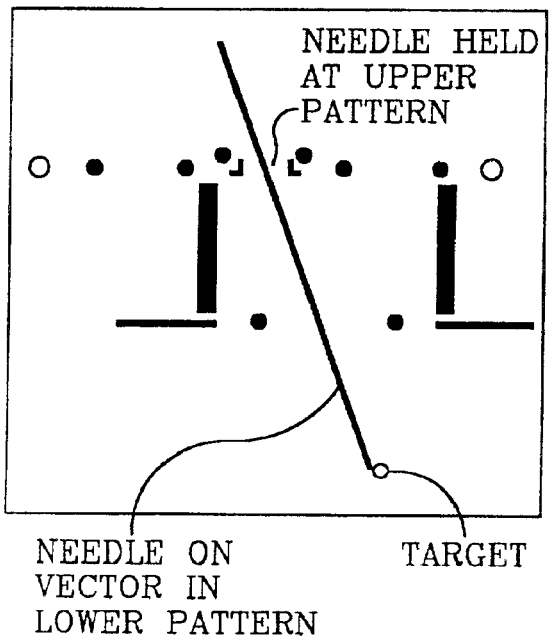

STEP 4:
PLACE NEEDLE IN CORRECT MEASURED POSITION ON LOWER PATTERN, POP NEEDLE IN UPPER SUPPORT V.

STEP 5:
MEASURE DISTANCE UPPER PATTERN NEEDS TO BE MOVED RIGHT-LEFT AND MAKE REMOTE ADJUSTMENT.

STEP 6:
MOVE NEEDLE (REMOTE) TO MEASURED SLICE LOCATION ALONG TOP PATTERN AND CONFIRM CORRECT LOCATION WITH MIDDLE V PATTERN.

STEP 7:
MEASURE DISTANCE FROM NEEDLE TIP TO TARGET.

FIG-26

NEEDLE DIRECTED TOWARD TARGET   TARGET

STEP 8:
CONFIRM THAT ACTUAL NEEDLE POSITION IS ALONG VECTOR PATH, IF NOT MAKE MINOR ADJUSTMENTS USING REMOTE mm SCALES.

STEP 9:
HOLD DEVICE STEADY AND ADVANCE THE NEEDLE TO THE TARGET, YOU MAY PUSH THROUGH THE DEVICE TOWARDS THE TARGET WITHOUT INTERRUPTION.

STEP 10:
CONFIRM SUCCESSFUL PLACEMENT.

STEP 11:
REMOVE DEVICE.

STEREOTACTIC APPARATUS AND METHODS

This is a divisional application of U.S. application Ser. No. 09/394,585, filed Sep. 13, 1999, now U.S. Pat. No. 6,406,482. The aforementioned application is herein incorporated in its entirety by reference.

TECHNICAL FIELD OF THE INVENTION

This invention relates generally to apparatus and methods useful in scientific research and interventional medicine, and useful in the visualization and analysis of organic tissues and bodies; and to research into the cause and symptoms of disease, its diagnosis and treatment. The invention particularly concerns apparatus which may be advantageously utilized by a researcher, physician or health care professional, in cooperation with cross-sectioning types of medical imaging equipment, such as computed tomography (CT) imaging equipment or magnetic resonance (MR) imaging equipment, plain film or fluoroscopy. The invention may be utilized to conveniently and accurately aid in timely (real time), manually, truly, and physically accomplishing the steps of locating, vectoring, and inserting an object such as a probe or other needle-like medical device at, toward, and in a patient's targeted anatomic feature.

BACKGROUND OF THE INVENTION

This invention relates to magnetic resonance apparatus useful in the visualization and analysis of organic tissues and bodies, and to research into the cause and symptoms of disease, its diagnosis and treatment.

In the use of magnetic resonance imaging ("MRI") there is a serious problem with interventional procedures. The problem is that the probe cannot be seen, and therefore its location is unknown at the moment before it is to enter the patient. This is one of the most important reasons why MRI has not been used extensively for interventional procedures.

There are many imaging stereotactic devices currently available. Despite the incredible power of existing imaging technologies however, very few procedures are actually done using the existing technology in a routine clinical setting. There are several reasons for the lack of general acceptance of these devices in existing markets.

Most of the systems are expensive, and normally this expense cannot be justified in terms of usage or benefit for the large capital investment required. Physicians and hospitals are generally not prepared in today's economic climate to make a large investment for a system that may only be used intermittently and may become quickly outdated.

Most existing systems are electronic and use optical and computer interfaces. The majority of these systems do not function in a real-time setting, but rather use special post-processed acquired image information. This information is then used to direct the procedure at a different time and place.

Many of the systems are imager proprietary or dependent, so it is possible that only a few units may be able to use a specific technology. Though these systems claim to have very high real-space accuracy, in reality, they have only limited real-space correlation since there is no live (real-time) imaging to confirm the progress of the procedure.

Most stereotactic units are complex and have multiple components. Some of the systems envelop the patient, for example, through the use of head frames that are bolted directly to the skull. If there is any change in the components of such a rigid system at the time and place of the actual intervention, the previously obtained information that forms the basis for the intervention is no longer valid. These systems also rely on gathering many images to direct the operation, rather than needing only a few. Because of this, the process can be very slow, since a large amount of data needs to be acquired to direct the process.

A number of existing stereotactic systems utilize fiducials that are placed on the patient or the stereotactic frame. These are image-conspicuous markers that are seen in the image space and real-space. Utilizing this information, the virtual reality space depicted on the images is fused with the real-space.

There are a number of devices that attach directly to the scanner, but these are generally cumbersome and have not been used extensively.

There are also a few systems that use very limited vector trajectories (of only a few angles). These are of little value since the limited number of approaches they provide to the target may not be enough to address the complicated anatomy, therapeutic devices and goals of a variety of procedures.

Currently there are a number of rapid CT or MRI data acquisition systems available, but they have the disadvantages of being proprietary and of exposing the patient and operator to increased radiation dosage. These CT systems are analogous to fluoroscopy.

There are a few combined CT and fluoroscopic stereotactic systems. These have the potential to be very versatile, but they are complex proprietary systems. There are also a number of open magnet designs, but these are limited by vendor design. Critical information used to direct the procedure or intervention is based on artifacts from the needle or probe rather than on accurate real-time real-space information. The inherent imaging problems created by these artifacts limit the accuracy of these devices. The image quality of the fast imaging systems in general is not as good as routine imaging techniques.

FIG. 1 is a schematic of an enveloping frame that is used for head stereotactic systems of the prior art. The vertical lines 1 of the box represent the vertical struts, the horizontal lines 2 are crossing members used to define the section plane, the angled lines 3 represent cross-members and the sphere 4 is the target. This frame is bolted or rigidly fixed to the patient and then imaged with many sections. The information gathered is used at a later time and place. Without real-time real-space confirmation during the intervention, there is no absolute confirmation that the previously determined plan is actually being correctly implemented.

FIG. 2 is a schematic of an image obtained from such a fixed frame rigid system. The vertical members 1 are seen at the corners of the square, and the cross-members 3 are used to define the slice location and the target 4. There is no intuitive information that an operator can use to confirm that the information is accurate. Typically, a second system is used to actually execute the procedure at a later time with no real-time real-space confirmation of the previously obtained plan.

FIG. 3 shows an example of an MRI image 5 showing the use of a fixed frame stereotactic unit used for head imaging. The head 6 appears in the center of the image, with the target labeled in the left temporal bone. Also visible are the rods 7 (such as horizontal, vertical and cross-members 1, 2 and 3 shown in FIG. 2) surrounding the skull of the patient as a fixed device. The information is acquired by taking multiple images that must be post-processed.

There are a number of limitations to this type of device. The constituent support tubes are necessarily relatively large (in order to support the static arrangement), and thus cause a certain degree of inherent error in the system. The image shown is a single image that provides no real-time information that an operator might use during an image-monitored procedure. Also, a further error factor arises because the tubes are relatively distant from the target site, and the image itself is not without distortion, making the system distortion sensitive. Also, if the subject is moved, the system cannot be readily realigned.

A number of computer-based systems' disadvantages have been mentioned. The most important of these is that they provide no real-time confirmation at the actual time of intervention. All of these systems use specially acquired post-processed images that assume that the virtual reality of the previously obtained imaging information and the true reality at the time of the actual intervention are identical. These systems are expensive, large, and can only be used in select locations.

There remain problems associated with fast, open, and combined technology systems. All are expensive, vendor specific and, as such, are limited to only a few sites. They are such complicated systems that any minor problem can render them useless, for example, if the batteries on an LED stop working. They have limited real-space accuracy since they have problems with partial volume averaging and other imaging artifacts. Using these systems it may be difficult to track more than one device being used at a time.

Accordingly, the criteria for an improved stereotactic device included:
1. Accuracy in the form of mm level control and live image confirmation.
2. Ability to make rapid adjustments (preferably by remote control), and the use of a single image.
3. Flexibility in the form of multiple dimension adjustability, and the accommodation of a wide variety of probes.
4. Intuitive use through clear, non-computer-generated interpretation of electronic image information.
5. Simple construction; a device that may be compact enough to fix the imager on the patient and inexpensively constructed, and may be of disposable materials.
6. Applicability independent of site and imaging device.

Accordingly, there remains a need for relatively inexpensive stereotactic devices that may be used with a wide variety of imaging systems for the performance of varied procedures, and that may be used with any number of invasive devices and techniques.

SUMMARY OF THE INVENTION

The present invention includes stereotactic vectors, no electronic calculations and imaging, diagnostic and treatment techniques.

In broadest terms the stereotactic device of the present invention comprises:

A stereotactic device comprising a frame portion attached to: (i) a lower plane portion defining a lower plane and comprising a lower vector point, the lower plane portion comprising a template comprising at least one pair of angled members of an imager-conspicuous material, the at least one angled member defining an angle of about 53 degrees; and (ii) an upper plane portion; the upper portion comprising: (1) a template defining an upper plane and comprising at least one (preferably a pair of) adjacent angled members comprising an imager-conspicuous material, the pair of adjacent angled members aligned such that the pair of adjacent angled members open in substantially parallel directions, and wherein the angle defined by each of the pair of adjacent angled members defines an angle of about 53 degrees, and (2) an alignment structure comprising an upper vector point adapted to move parallel to the upper plane, so as to be able to define a vector passing through the upper and lower vector points.

It is preferred that the stereotactic device have adjacent angled members that include a graduated linear distance position scale perpendicular to its bisector line.

The principal V patterns of the lower plane position may be accompanied by additional adjacent V patterns representing equidistant graduations from the respective main "V" limbs.

The lower plane portion may also include a template comprising at least one pair of angled members of an imager-conspicuous material defining an angle of about 53 degrees. Preferably, two pairs may be used for alignment purposes as described below.

Preferably, the frame portion is adapted to rotate the upper and lower plane portions with respect to an axis perpendicular to the upper and lower parallel planes. It is further preferred that the frame portion additionally comprise a graduated position scale to indicate the degree of rotation of the upper and lower plane portions parallel with respect to one another and in an orthogonal motion.

The stereotactic device of the present invention may optionally include at least one remote actuator to move the alignment structure within the upper plane (i.e., in the X and Y directions as described herein). Likewise the stereotactic device of the present invention may optionally include at least one remote actuator to rotate the upper and lower planes with respect to one another.

In one embodiment, the stereotactic device may have a lower portion provided with an adhesive base portion.

The stereotactic device of the present invention preferably includes an alignment structure in its upper portion that has an interior area through which at least portions of a medical instrument may be passed.

The alignment portion may further include an addition V pattern that bears a graduated linear distance position scale.

The imager-conspicuous material may be selected from any material appropriate to the imaging device. These may be selected from the group consisting of metal members, hollow polymeric members filled with an imager-conspicuous material, and polymeric members treated with an imager-conspicuous material.

The lower plane portion may be connected to a band (preferably elastic) to be held in place. It may also be connected directly to a sterile or sterilizible drape material to protect the target surface from contamination, such as where an adhesive is used to hold it in place. Alternatively, the lower plane portion may be connected to an elastic band, and the elastic band attached to the drape material. These arrangements may be formed though the use of stitching, adhesives, or other techniques known in the art for attaching elastic, drape materials, such as cloths or polymeric materials, and rigid plastics, foam or other solid materials, to one another.

In another embodiment, the stereotactic device of the present invention may feature an open architecture to allow the lateral, parallel and orthogonal motion removal of a probe from the device once aligned. The stereotactic device of this embodiment of the present invention comprises: a frame portion attached to: (i) a lower plane portion defining a lower plane; and (ii) an upper plane portion; the upper plane portion comprising: (1) a template defining an upper plane and comprising a pair of sufficiently adjacent angled members comprising an imager-conspicuous material, the angled members aligned such that they open in substantially parallel directions, and wherein the angle defined by each of the pair of adjacent angled members defines an angle of about 53 degrees; and (2) an alignment structure adapted to move within the upper plane, so as to be able to align a vector passing through the upper and lower planes. In this embodiment, the alignment structure comprises a releasable alignment aperture, such as one made up of opposed flexible members that cooperate to form the alignment aperture. It also includes a frame portion that is open on one side so as to allow an object passed through the alignment structure to be removed in a direction substantially parallel to the upper plane.

In this embodiment the portions of the device, such as the lower portion and the frame portion, may also be as described in their many variations above.

The present invention also includes an alignment article for use with an imaging device (such as used as a lower template portion as described herein). The alignment article comprises an imager-transparent member bearing an imager-conspicuous material in the shape of at least one angle of about 53 degrees. The imager-conspicuous material may be, for instance, in the form of printed material or plastic tubes filed with imager-conspicuous material and adhered to the article. In one embodiment of the article, the alignment article may be planar and additionally comprise an adhesive base on one side thereof. Preferably, the alignment article has at least one angle additionally comprising a graduated linear distance position scale perpendicular to its bisector line. The alignment article may also have additional adjacent "V" patterns for equidistant graduation from the respective main "V" limbs. In another embodiment, the alignment article is planar and bears imager-conspicuous material in the shape of two angles each of about 53 degrees and open in substantially parallel directions, and additionally comprising a perforation in the article passing between the two angles. It is preferred that the alignment article comprises a material capable of being perforated by a syringe needle.

The present invention also includes the methods of placing a probe from outside a tissue (or other matter) into a target area located within the tissue (or other matter) using an orthogonal drive imaging device, where the target area is within reach of a probe from a targeting surface of said tissue, said method comprising: (1) establishing a lower plane substantially at the surface of said tissue, the lower plane comprising a lower vector point, and the lower plane portion comprising a lower plane template comprising a pair of angled members of an imager-conspicuous material, each of said pair of angled members defining an angle of about 53 degrees; (2) establishing an upper plane above the surface of the tissue, the upper plane comprising an upper plane template comprising a pair of adjacent angled members comprising an imager-conspicuous material, the pair of adjacent angled members aligned such that the pair of adjacent angled members open in substantially parallel directions, and wherein the angle defined by each of said pair of adjacent angled members defines an angle of about 53 degrees, (3) providing an alignment structure comprising an upper vector point adapted to move parallel to said upper plane, so as to be able to define a vector passing through said upper and lower vector points; (4) if not so aligned, aligning the upper plane and lower plane templates such that the image plane of the imaging device is aligned perpendicular to the bisectors of each of the adjacent angled members; (5) determining the position of the target area with respect an entrance point through the lower plane template, (6) adjusting the alignment structure so as to form a vector containing said entrance point and a point in said target area; and (7) passing the probe along said vector to the target area.

The device and methods of the present invention may be used with any diagnostic or clinical imaging device, such as MRI, CT, radiographic or fluoroscopic devices. The device and methods of the present invention may also be used with industrial imaging devices in fields even outside of life sciences and medicine.

The device of the present invention is based on a unique image pattern that encodes exact dimensional information (e.g., in mm) on each image that is directly related to the identical dimensional positions (e.g., in mm) in real-time and 3D space. This means there is no need for computers or any other type of complex translation of the image information to utilize data in the real-time space of the image system.

For example, if the image generated by the device depicts two dots separated by 41 mm, this means that image section plane is crossing the image conspicuous pattern of the device at a line labeled 41 mm on the device in real-space.

In a real-time environment, the visual cues generated by the device-generated pattern lead the operator to an exact real-time space location without the need of special computer information. For example, if the operator is moving the correct direction, the pattern displays points converging. If the operator is moving the wrong direction, the points diverge.

The pattern generated by devices of the present invention, in its preferred embodiment, is based on a specific geometric oddity. A triangle formed in a square has this property when the base of the triangle is the base of the square and the apex of the triangle is the midpoint of the top of the square. The triangle formed in this specific situation is a special isosceles triangle of about 53 degrees. The pattern of the preferred inventive device uses the limbs of this triangle. The limbs of the preferred device pattern are made of image conspicuous materials.

When the imaging section plane is parallel to the pattern it produces a set of unique imaging and real-space characteristics.

The true distance between the limbs of the device image conspicuous pattern as measured on the image is equal to the true distance from the intersection of the pattern limbs. There is no need for a computer to tell the operator when this occurs or for complex calculations. The slice location is encoded as a true linear measurement on the image.

The distance from a limb of the device's image conspicuous pattern to a vector line measured on the image can be used to define the same point in real-space on the device.

FIG. 4 shows examples of the stereotactic pattern generated by a device in accordance with one embodiment of the present invention.

The "V" shapes represent the device-generated pattern. The angle of the "V" shape should preferably be about 53 degrees.

The device pattern has a unique characteristic. The distance between the limbs (horizontal arrows 8) of the pattern measured on the image when the slice symmetrically crosses the pattern (parallel to the base of the triangle) is equal to distance from the intersection of the two limbs (i.e., the distance along vertical arrows 9). Note that independent of where the image slice crosses the pattern, the distance from the intersection of the two limbs is encoded on the image by the pattern being of an image conspicuous material. This relationship allows for immediate exact definition of the location of the section plane in real-space on the pattern using only this simple image information.

For instance, when using CT, each limb of the "V" may be made of an image conspicuous material such as wire. In the case of MRI, tubes (typically non-metallic; plastic) filled with contrast enhanced fluid may be used as pattern limbs. The pattern may also be drawn directly on the patient, or included on an imager transparent material attached to the patient, such as through the use of adhesives. Examples may include a piece of flexible material, such as Mylar, provided with an adhesive on one side and bearing an image conspicuous pattern (provided in the form of an attached image conspicuous object in the shape of the "V", or in the form of a printed design in the shape of the "V" in accordance with the present invention). Another example may be an adhesive strip, similar to an adhesive bandage, and provided with image conspicuous material members attached thereto, or an image conspicuous "V" pattern printed thereupon.

FIG. 5 shows a view of two V-shaped patterns adjacent to each other, forming a "W"-like pattern. The two upwardly-opening triangles represent the necessary image-conspicuous components of the present invention. The pattern is sectioned at various planes. The image plane is parallel to the base of the pattern. Section A is at 30 mm, B is at 10 mm and C is at 0 mm in relationship to the pattern. The images produced at each section are shown in FIG. 6.

FIG. 6 is a view of the image perspective of each slice shown in FIG. 5. This view, and that shown in FIG. 5, shows how the points on the image diverge with the true distance of the image section plane from the base of the pattern (such as the distance of planes 11A, 11B or 11C from the intersection of the "V" limbs). For instance, section 11A is at 30 mm, 11B is at 10 mm and 11C is at 0 mm in relationship to the pattern. When the distances between the image plane intersection points 14 of each pair of "V" limbs are equal, the image planes 13 are determined to be parallel to the base of the pattern (i.e., perpendicular to the bisectors of the two "V" angles).

The distance between each limb of the pattern encodes the slice location in millimeters in the same dimension on the pattern as is seen on the image. The distance between the points on each "V" is identical, confirming that the image plane is parallel to the device. With this information, a plane on the pattern can be found or the image slice can be moved to a precise position in relation to the pattern. For example, if the distance between the intersection points of the image plane 13 with the limbs of each V was 10 mm, but the operator wanted to move the patient to the 30 mm line on the device, the operator would know how many millimeters, and also in which direction to move the table on which the patient may rest. Likewise, the operator may also move the intended insertion point of a medical device, such as a needle, diagnostic probe or any other therapeutic apparatus (such as any object, directed matter or light) that may be directed toward the target point along a vector determined by the device of the present invention.

Thus, one of the fundamental features of the device is that it provides a three-dimensional alignment template that resides at a distance from the identified target point without having the target point located within the space defined by the three-dimensional alignment template. This allows the three-dimensional alignment template to be repositioned and to function accurately even if the tissue or patient has moved. FIG. 6a is a graphical representation of a demonstration of these optional angulation properties. Two V patterns are shown with various parallel section planes shown crossing the device pattern. The distance between each V (V1 and V2) is labeled for each image section. Note that the linear distance measurement differences between these two is always the same. In this case, V1−V2 equals −7. The value is related to the angle that the slice and pattern define with their intersection, and it is independent of the location of the section. The sign (positive or negative) encodes which direction the pattern must be rotated to achieve alignment. The value and sign are printed on the device; similar to a degree scale (in V1−V2 units), so the operator may rotate the device to the precise parallel position from a single image acquisition. This is done at the beginning of each procedure to confirm appropriate positioning of the device.

FIG. 6b shows a graphical representation of a diagram illustrating mathematical difference between V1 and V2 (on the right) and the increasing mal-alignment in degrees (on the left) of the image plane to the pattern. It should be noted that V1−V2 is not a simple function of degrees, but is more complex. The actual degree scale in V1−V2 values may be printed on the device for accurate rotation of the device pattern to the section plane.

FIG. 7 shows a plan and a perspective view of the device-generated pattern. The points on the image diverge with the true distance of the pattern formed by the intersection of V1 and V2 with the image section plane 13, as seen by reference to the dots showing the intersection points of the image plane 14 appearing in the image view, and comparing this view to the geometry shown in FIG. 6.

FIG. 7a shows a plan and a perspective view of the device-generated pattern.

The section plane has been moved to a position closer to the top of the W formed by the two "V" patterns. In the bottom figure, it can be seen that the section plane 13 intersects V1 and V2 such that the points of intersection 14 are further apart. When aligned so that the distances between the intersection points of each "V" are the same, the distance between the intersection points 14 of each "V" corresponds to the distance of the section plane from the plane containing the points of intersection of the limbs of the two "V" figures. The distance may be represented on a scale that may be printed on the device to provide for precise localization in real time without the need for computer information.

FIG. 7b shows a plan and a perspective view of the device-generated pattern, as it would appear when the section plane and the pattern of the device of the invention are not parallel. This view shows that the intersection points 14 of the section plane 13 on V1 are closer together than those points where the section plane 13 intersects V2. The differences between these two distances can be used in calculations that allow the device to be quickly aligned with the section plane.

FIG. 8 shows a view of two V-shaped patterns 10 (also designated separately V1 and V2) adjacent to each other, forming an "M"-like pattern, to illustrate the operation of a device in accordance with the present invention. The triangles represented by these V's are portions of the device pattern that represent the required image conspicuous components of the device pattern (other portions may be made image conspicuous as desired). The two-V pattern allows the operator to determine whether the device is parallel to the image plane 13 by assuring that the intersection points of the image plane 13 with the respective limbs of V1 and V1 are equidistant.

The pattern is preferably ruled so as to section the device scales at various planes 11 along at least one axis of the device pattern, preferably perpendicular to the bisectors of V1 and V2, so as to provide a measure of the distance from one edge of the device pattern (i.e., where the legs of each V intersect) to the opposite edge. This provides a reference template to locate a target point (i.e., target point 12) within the imager view and with respect to the legs of the V scales 15.

The pattern may also include multiple smaller "V" scales 15 of similar geometry as shown in FIG. 8. These additional patterns are designed so that the distance from any of the other principal "V" limbs can be determined. In the embodiment shown in FIG. 8, the multiple smaller "V" pattern scales 15 are spaced such that they represent increments of millimeters.

FIG. 8 also shows the preferred circular shape imposed with respect to the device pattern, and the graduated scale 16 that measures the degree to which the device pattern may be non-aligned with the image section. This graduated scale is expressed in terms of V1 minus V2 representing the difference of the distance between the image plane intersection points on V1 and the distance between the image plane intersection points on V2.

FIG. 8A shows a CT plan view of a device pattern, showing the image slice location 13 and target point 12 located, in this example, 41 mm from the base of the image pattern (i.e., the line where the legs of each V intersect; determined by knowing the distance between the intersection points of the image plane with the legs of one of the Vs). This value may be read from the linear scale 17 provided along the side of the rectangle enclosing the dual V pattern. In the position shown in FIG. 5A, the distance from the inner V limb of V1 (i.e., the V within which the target point is found) is 13 mm. This distance may be determined by referencing the target point as it appears between the limbs of two of the smaller Vs, within the principal V1 pattern, that represent, respectively, 10 and 20 mm from the inner V limb of V1, (i.e., the target point is about 13 mm from the inner limb of V1).

FIG. 9 shows the operation of the graduated scale 16 that measures the degree to which the device pattern may be non-aligned with the image section. In this example, the image on the left shows that the device pattern is displaced with respect to the image plane, indicated by the V1 distance being 19 mm and the V2 distance being 31 mm. The graduated scale shown below the device pattern is expressed in terms of V1 minus V2 representing the difference of the distance between the image plane intersection points on V1 and the distance between the image plane intersection points on V2 In this case, the device pattern is rotated by negative 12 units to bring, easily and quickly, the device pattern parallel to the image plane (as shown in the image on the right of FIG. 9). The measured distance is independent of the slice thickness.

The pattern is preferably mounted onto a circular base so it can be rotated parallel to the section plane as directed, for instance, by reference to the circular graduations shown in FIGS. 8, 9, 11 and 15 that may be provided on a portion of the base or frame about which the two-V bearing template frame may be rotated.

The images produced at each section are shown in the FIG. 10. In this example, the target point is 13 mm to the right of the left limb of the V1 pattern at the 41-mm line from the intersection point of the limbs of the "V"s (note radiology right-left standard labeling). The image plane is centered at the 41-mm line. The lines parallel to the image conspicuous device pattern may be used to find the precise point on the pattern in real-space. These are not visible on the image.

The image on the upper right of FIG. 8A is a scout plan image of the same pattern. The two pattern limbs ("V"s) are seen and the circle encloses the target point. The image plane intersects the pattern at the 41-mm line, and this distance is the same as that from the intersection of the two limbs. FIG. 10 shows an image perspective of the same pattern and target point seen in FIG. 8A (plan view on the left and real-space view on the left). Each "V" pattern limb is labeled. The demonstration target point is seen as a vertical density. The circle shows the target point. The distance measured on the image between each of the limbs of the V's is 41 mm, defining the location of the image plane on the device pattern. The target point is 13 mm to the right of the left limb of the right V1 pattern. Using this precise information, it is possible to place a small disc directly over the target despite the fact that the target is hidden from the view of the operator.

A small wire may be imbedded into a foam base below the opaque pattern to act as a point target for demonstration purposes as seen in FIGS. 8A and 10. The target point is centered in the small circle shown in the image.

FIG. 11 is an image view of a localized target point. FIG. 11 shows a view of the target point that has just been localized with a small plastic disc marker 17 placed over the target point in real-space at real-time in the scanner. This example shows that the localization of the target point with a high degree of accuracy. A skilled operator accomplished this localization in only a few minutes. Two small densities of the disc are seen directly overlying the target point. The disc was set at the 41-mm image section line and 13-mm from the left limb of V1. This is a simple example that confirms the speed and accuracy of a device of the present invention.

FIG. 12 shows image perspectives showing an example of how a device of the present invention, and the image information, is used in an actual imaging setting. The image on the left of FIG. 12 is a CT cross-section of the "V" pattern of the device shown earlier. The distance between the limbs of V1 is 19 mm (the smaller line on the left), and the distance between the limbs of V2 is 31 mm (the longer line on the right). It is clear that the device is not parallel to the image plane. The difference of V1 and V2 is −12 units. If the device is rotated this indicated degree and direction, the next image will be parallel to the image plane.

The image on the right of FIG. 12 is the plan view (real-space) of the pattern. It should be noted that it is clear that the section plane is not parallel to the pattern. The distances between the limbs of both V1 and V2 are shown as lines parallel to the section plane. A small target point is seen as a dot along the slice location.

Generally, devices in accordance with present invention may be accurate to within 1 or 2 units (i.e., mm or less) of the limits of the image resolution. These levels of accuracy may be achieved independent of the section thickness and orientation.

When an instrument is attached to a pattern device of the present invention, its position may be encoded independent of the slice thickness. Accordingly, partial volume artifact vector errors may be eliminated. The relationship of the instrument to the image may be encoded, a capability not possessed by known prior art devices.

FIG. 24 shows a stereotactic device of the present invention comprising: a frame portion attached or perpendicular to: (a) a lower plane portion defining a lower plane; and (b)

an upper plane portion comprising a template defining an upper plane and comprising a pair of adjacent angled members comprising an imager-conspicuous material, the pair of adjacent angled members aligned such that the pair of adjacent angled members open in substantially parallel directions, and wherein the angle defined by each of said pair of adjacent angled members defines an angle of about 53 degrees; the frame portion being open on one side so as to allow an object passed through the alignment structure to be removed in a direction substantially parallel to the upper plane.

The lower portion may comprise a template comprising at least one pair of angled members of an imager-conspicuous material, at least one angled member defining an angle of about 53 degrees. The frame portion may be adapted to rotate said upper and lower plane portions with respect to an axis perpendicular to the upper and lower planes. The frame portion may additionally comprise a graduated position scale to indicate the degree of rotation of the upper and lower planes with respect to one another. The lower portion may additionally comprise an adhesive base portion. The alignment structure of the upper portion may be perforable such that at least portions of a medical instrument may be passed. The adjacent angled members may further comprise a graduated linear distance position scale.

FIG. 13 shows an image perspective and graph showing the actual results of 10 point localizations with CT using a device of the present invention. In 95% of the cases the pattern was within 1.5 mm of the actual location. This has not been achieved through known simple sterotactic devices. When utilizing most CT imagers, the operator is able to actuate a laser positioning system to help localize the slice location. This can be helpful, but many times it may be inaccurate or of little value with live procedures because the light is obstructed. These laser-positioning systems are also frequently ineffective since the operator cannot work inside the bore of the system when the light is on to take advantage of its localizing capability. In MR systems, the laser positioning lighting systems are of even less value since they only define one or two limited planes. In fluoroscopic systems, the device may be used in accordance with the real time display, and thus it may not be necessary to use the device gradations, but instead, the device may still be used with its remote actuator while viewing the real time image.

In order to align the device with the section plane with sufficient accuracy and confidence, the device of the present invention may use its pattern to simultaneously encode the exact angle of alignment with the image plane in units that are printed on the pattern device for proper image section plane orientation. Based on the reading of these units, the operator may either rotate the device into alignment with the section plane or the plane may be rotated parallel to the device.

The ability of the device of the present invention to align the pattern to the image plane is possible because it is based on a number of unique mathematic and geometric relationships.

Independent of the location at which the section plane crosses the pattern, the mathematical difference between the dimensions in mm of the two V patterns (V1 minus V2) is a constant. Also, the mathematical difference between the distances of V1 and V2 (V1−V2) is constant for any slice at the same orientation to the pattern.

The mathematical difference between the distances of V1 and V2 (V1−V2) is proportional to the angulation of the section plane and the pattern.

This angle may be printed on the device in units of V1−V2 to enable the operator to rotate the device to the section plane for alignment. When V1−V2=0, then the pattern is parallel to the image section plane. The sign of V1 minus V2 (positive or negative) defines the direction of angulation (clockwise, counterclockwise). Either the section plane can be rotated to the pattern, or the pattern can be rotated to the section plane.

BRIEF DESCRIPTION OF THE DRAWINGS

FIG. 12 shows photographs of a cross-sectional image and a plan view of a localized target point, illustrating the results that may be achieved with a device in accordance with one embodiment of the present invention.

FIG. 20a is a perspective view of an alternative remote actuator that may be used in accordance with another embodiment of the present invention.

FIG. 20b is a perspective view of an alternative remote actuator that may be used in accordance with another embodiment of the present invention.

FIG. 25 is a photograph of an image perspective view illustrating a step in the operation of a device in accordance with one embodiment of the present invention.

FIG. 26 is a photograph of an image perspective view illustrating a step in the operation of a device in accordance with one embodiment of the present invention.

DETAILED DESCRIPTION OF THE PREFERRED EMBODIMENTS

Figure 1:
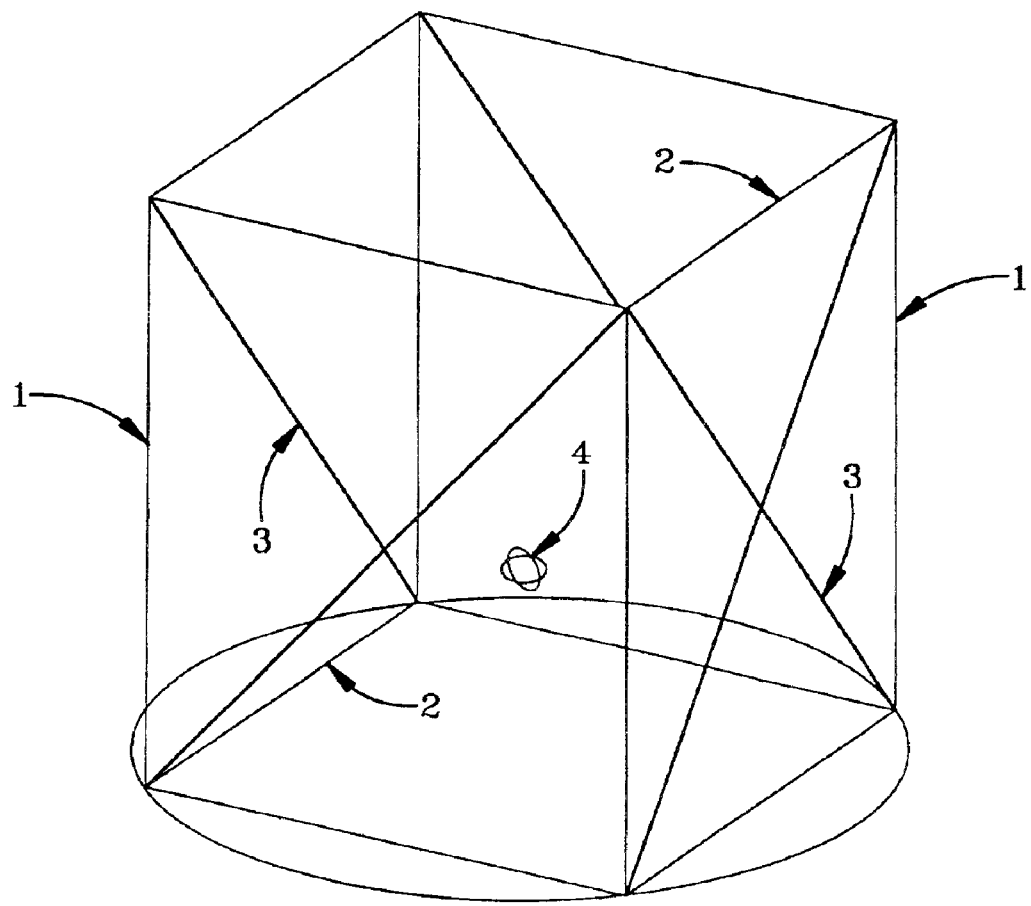
FIG. 1 is a schematic of an enveloping frame that is used for head stereotactic systems of the prior art.
Figure 2:
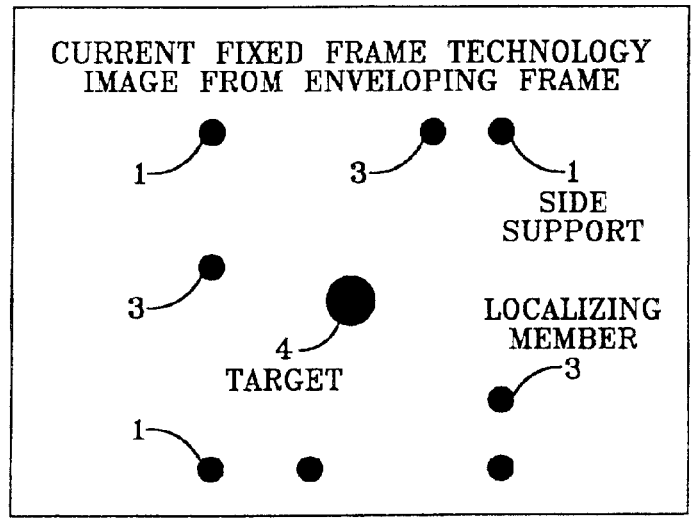
FIG. 2 is a schematic of an image obtained from a fixed frame rigid system in accordance with the prior art.
Figure 3:
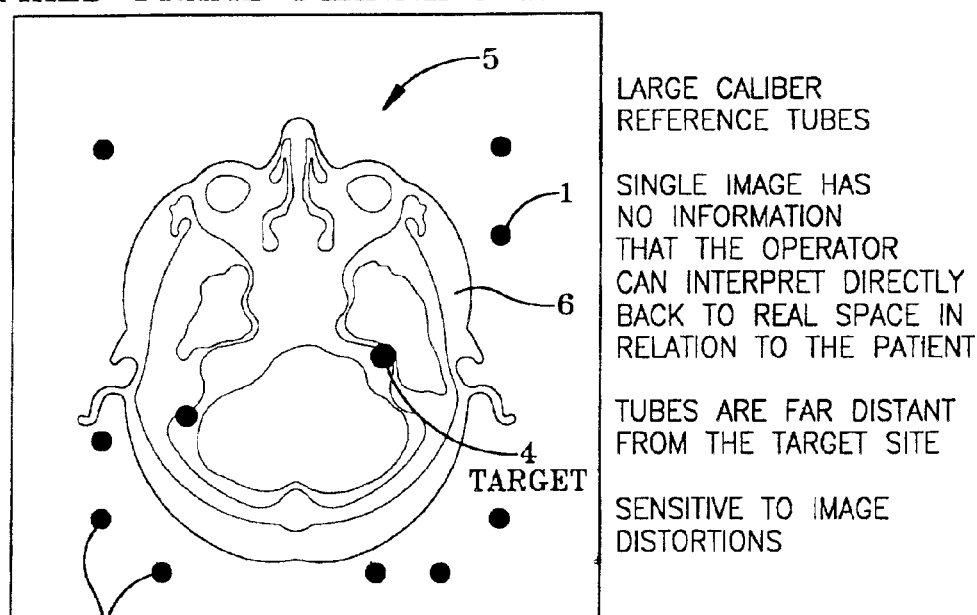
FIG. 3 shows an example of an MRI image showing the use of a fixed frame stereotactic unit used for head imaging in accordance with the prior art.
Figure 4:
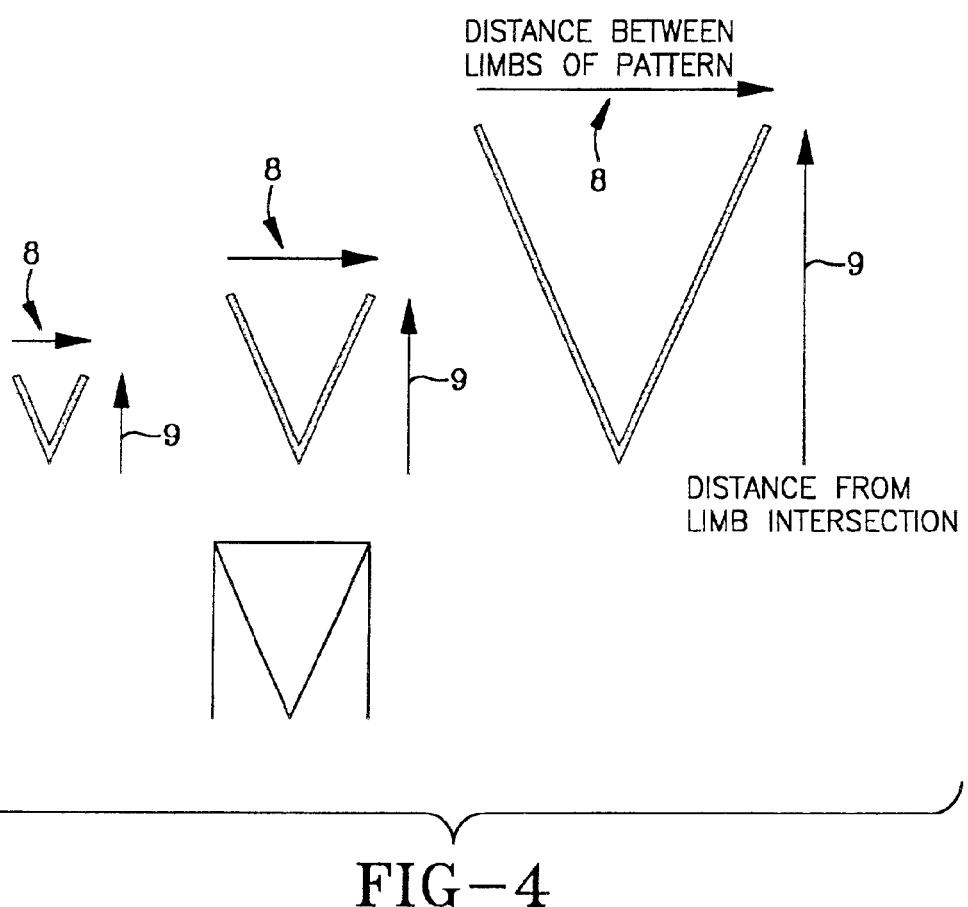
FIG. 4 shows examples of the stereotactic pattern generated by a device in accordance with the present invention.
Figure 5:
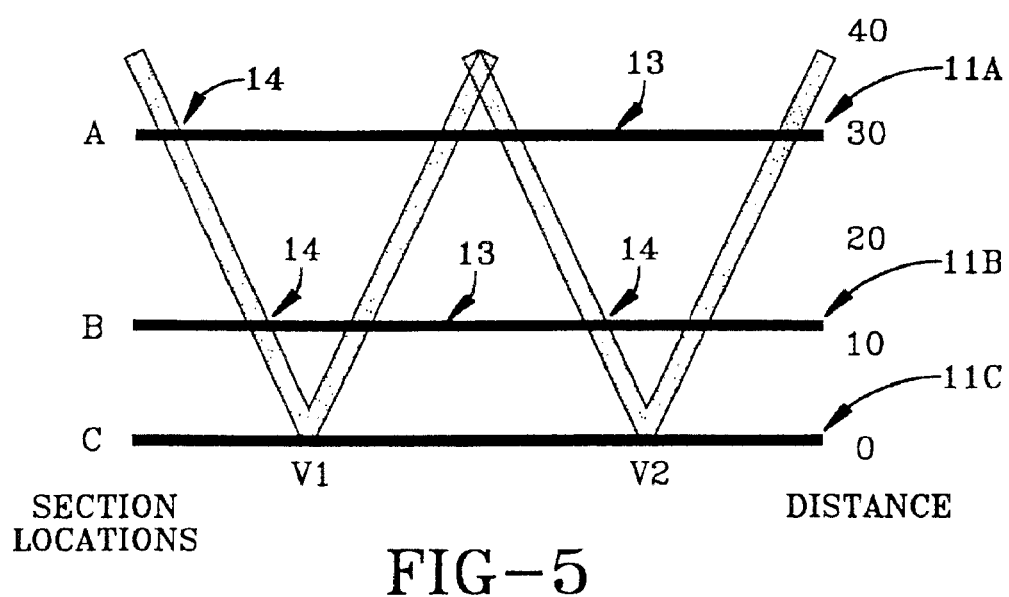
FIG. 5 shows a representation of two V-shaped patterns adjacent to each other, forming a "W"-like pattern, to illustrate the operation of a device in accordance with one embodiment of the present invention.
Figure 6:
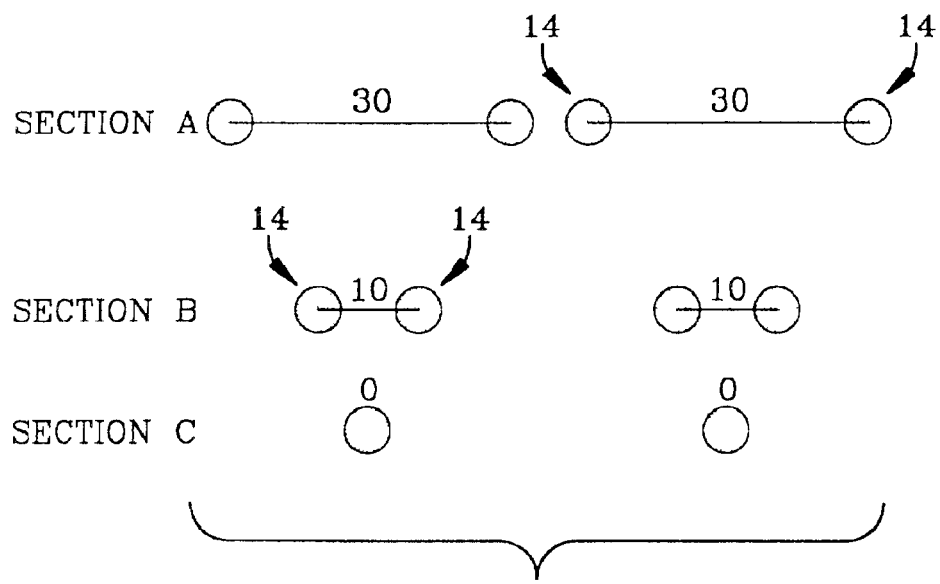
FIG. 6 is a view of the image perspective of each image slice representation shown in FIG. 5, to illustrate the operation of a device in accordance with one embodiment of the present invention.
Figure 6A:
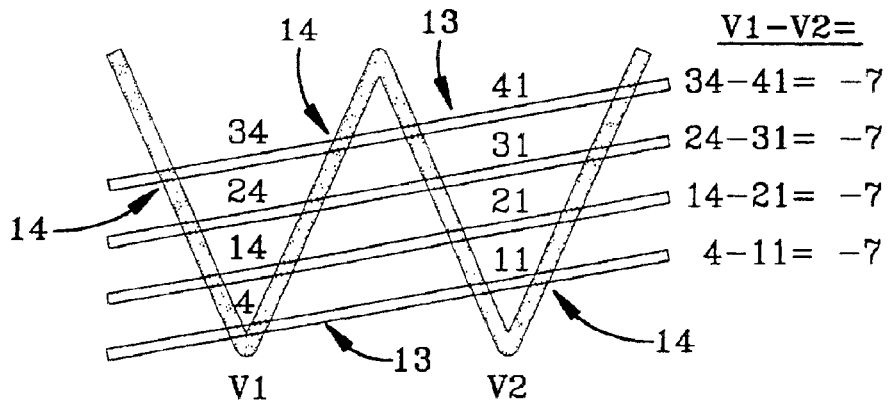
FIG. 6a is a view of the device-generated pattern, to illustrate the geometric basis of the operation of a device in accordance with one embodiment of the present invention.
Figure 6B:
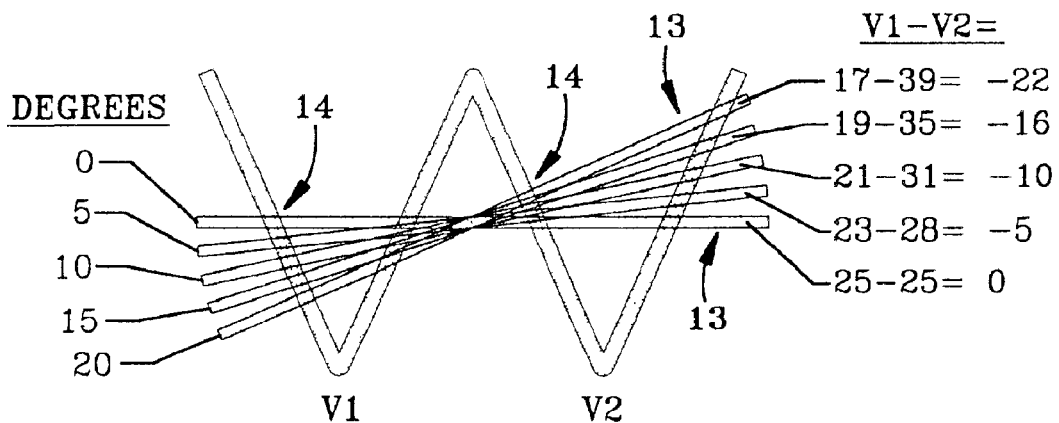
FIG. 6b is a view of the device-generated pattern, to illustrate the geometric basis of the operation of a device in accordance with one embodiment of the present invention.
Figure 7:
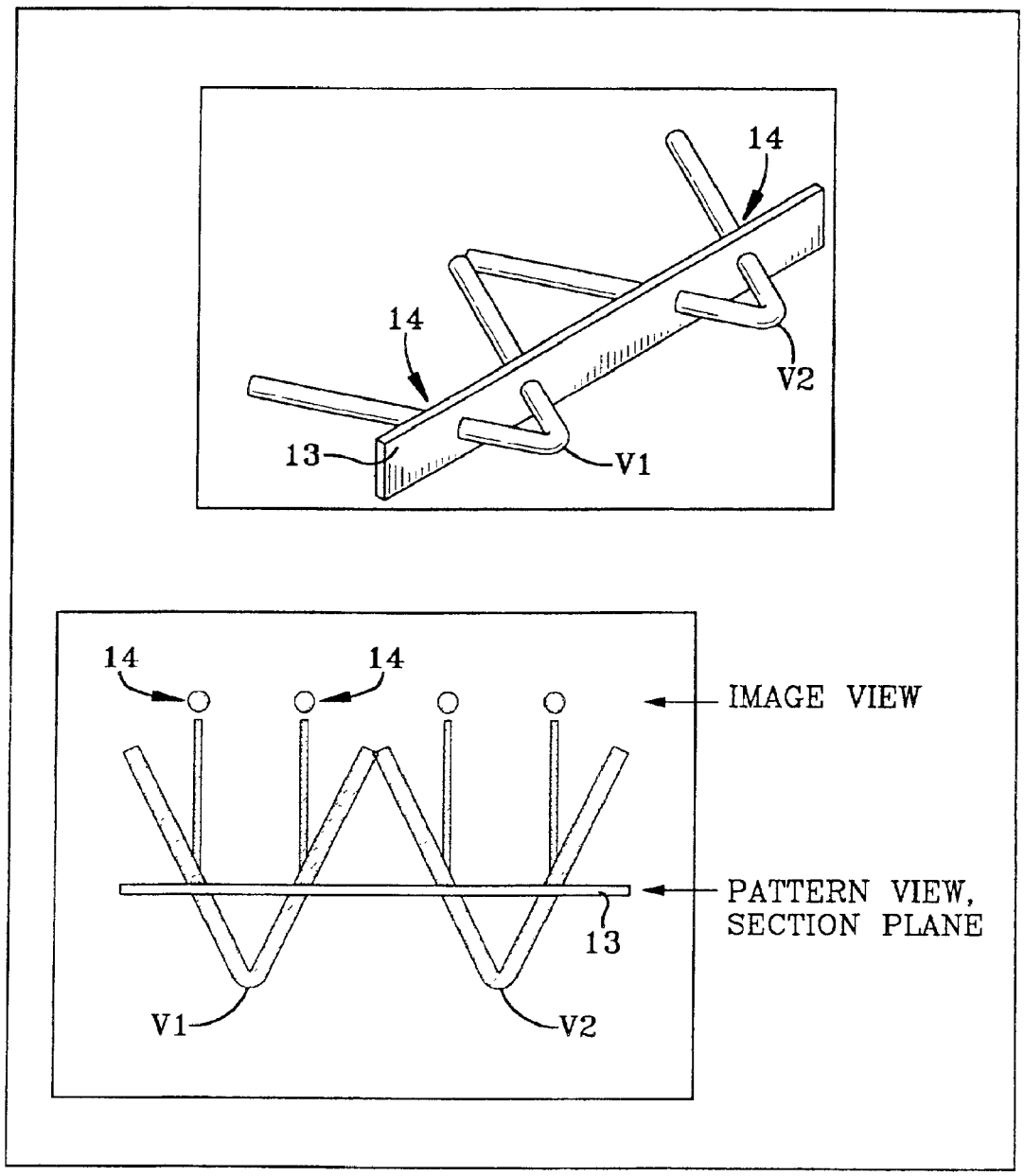
FIG. 7 is a view of the device-generated pattern, to illustrate the geometric basis of the operation of a device in accordance with one embodiment of the present invention.
Figure 7A:
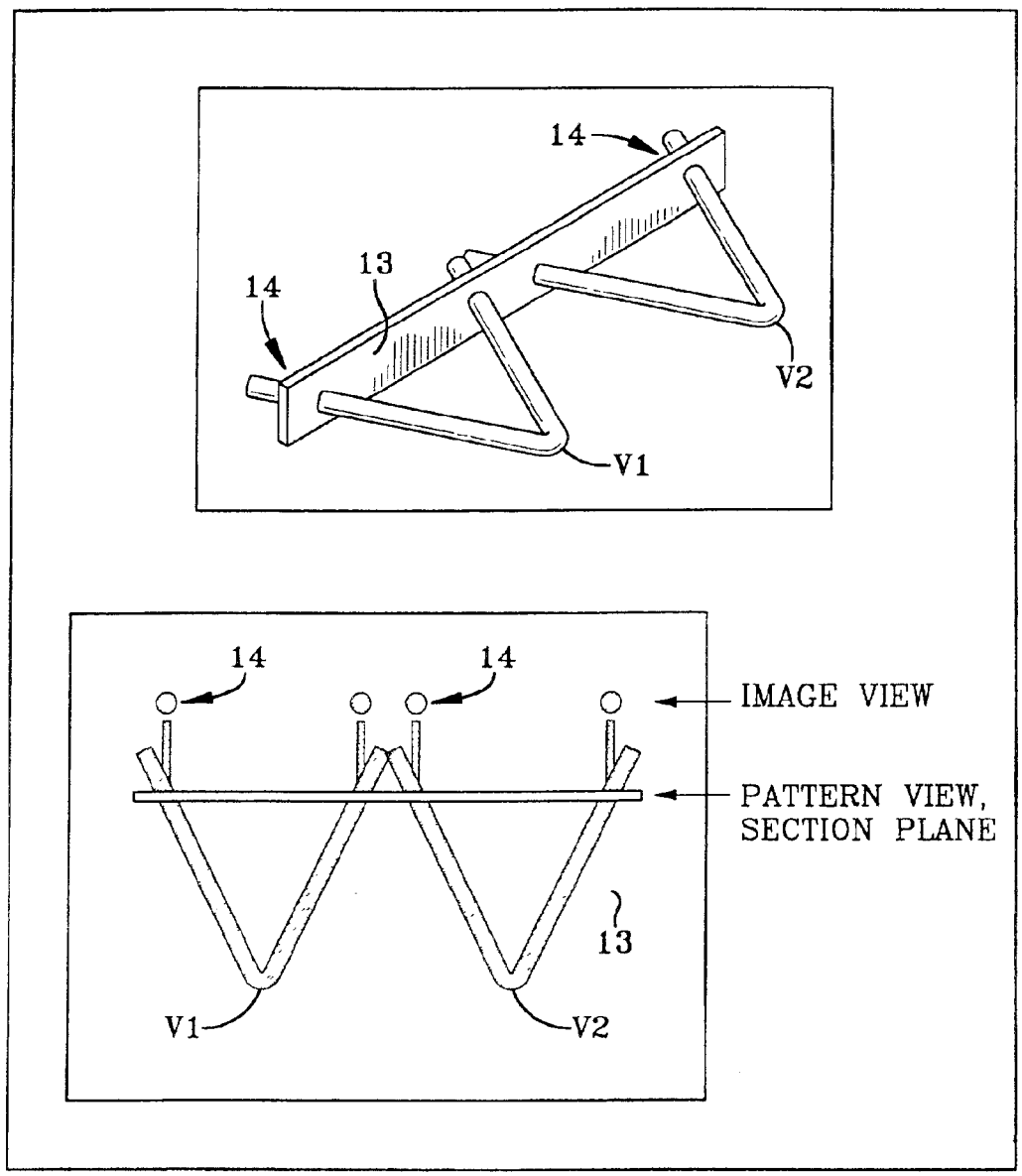
FIG. 7a is a view of the device-generated pattern, to illustrate the geometric basis of the operation of a device in accordance with one embodiment of the present invention.
Figure 7B:
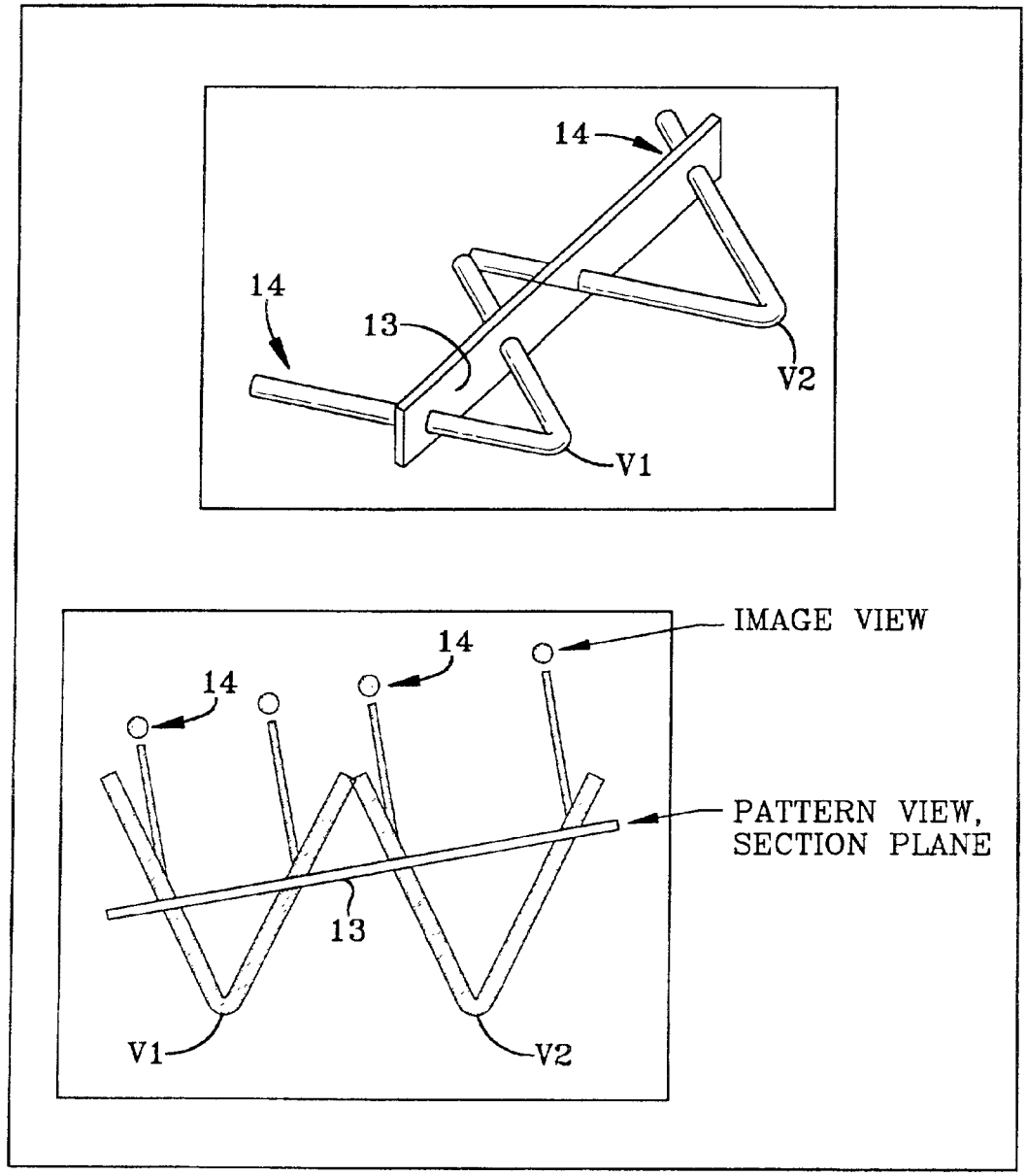
FIG. 7b is a view of the device-generated pattern, to illustrate the geometric basis of the operation of a device in accordance with one embodiment of the present invention.
Figure 8:
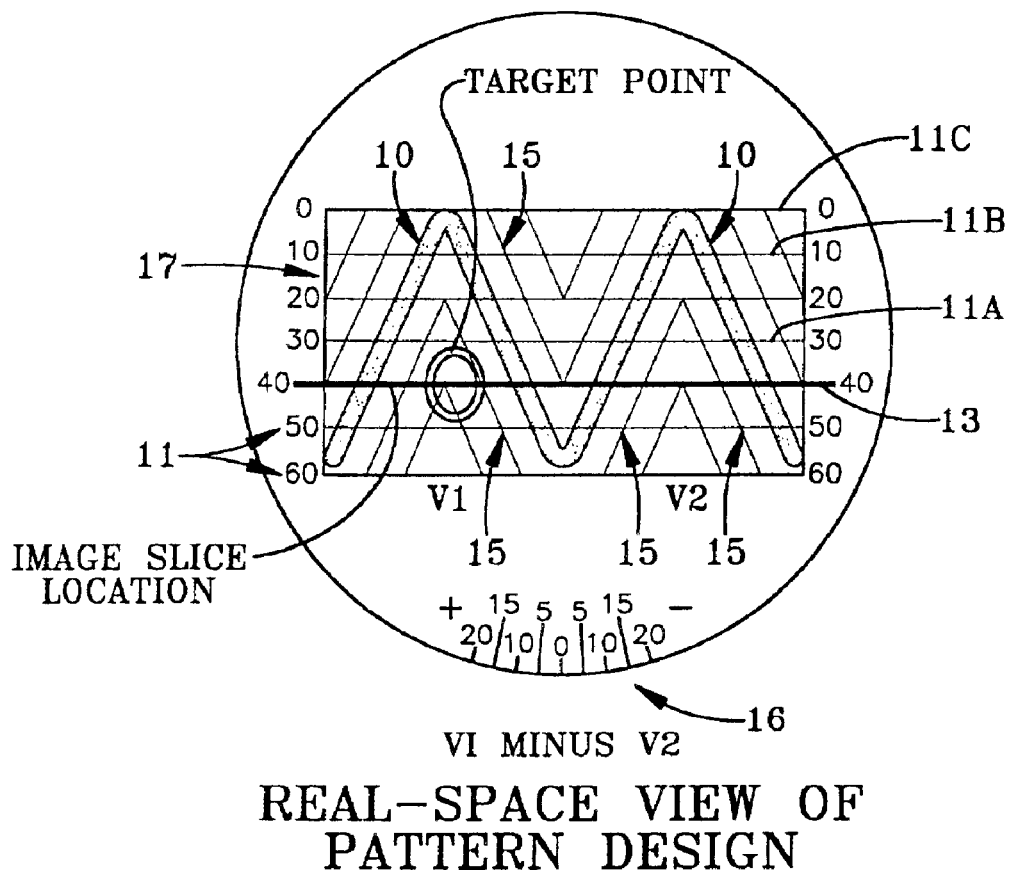
FIG. 8 is another view of the device-generated pattern, to illustrate the geometric basis of operation of a device in accordance with one embodiment of the present invention.
Figure 8A:
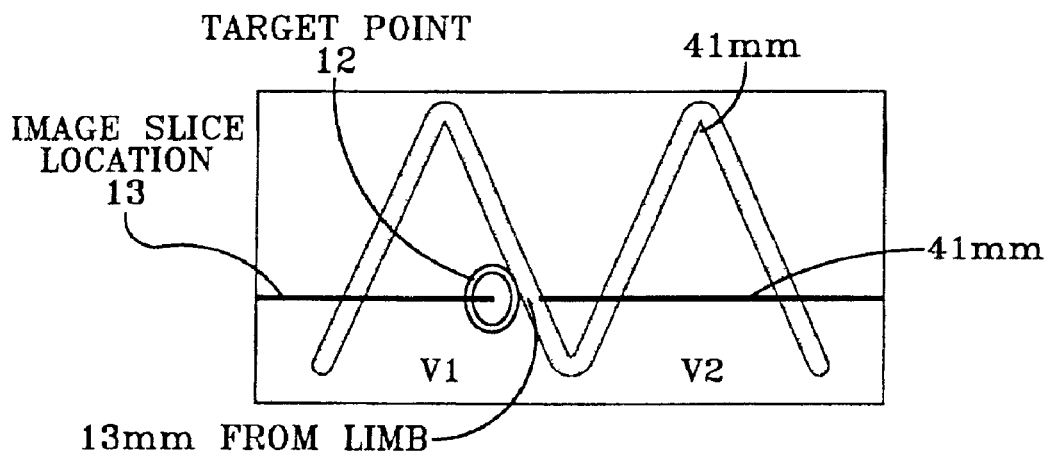
FIG. 8a is a CT planar image view illustrating the geometric basis of operation of a device in accordance with one embodiment of the present invention.
Figure 9:
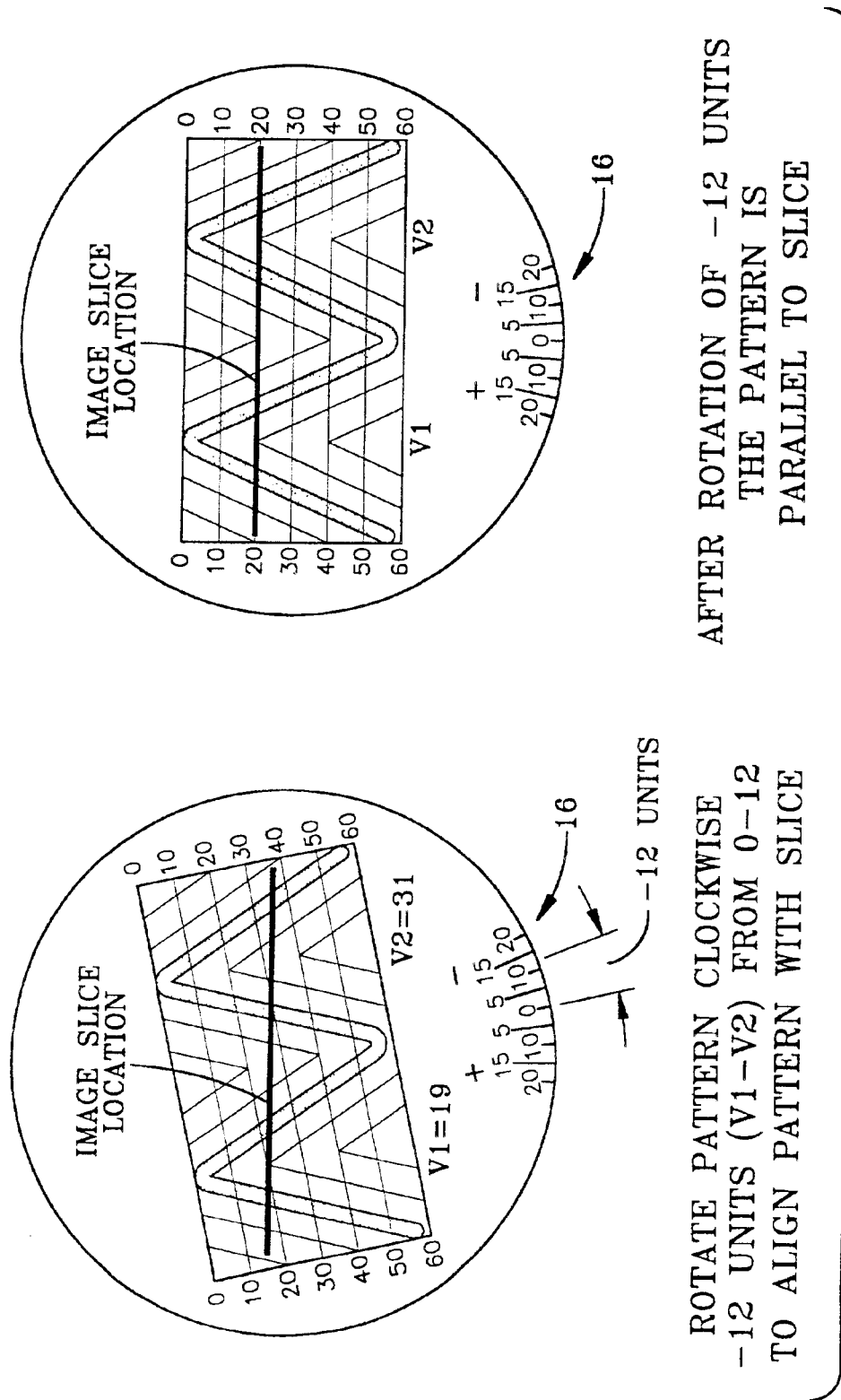
FIG. 9 is another view of the device-generated pattern, to illustrate the geometric basis of operation of a device in accordance with one embodiment of the present invention with regard to the rotation of the device to align it with the image plane.
Figure 10:
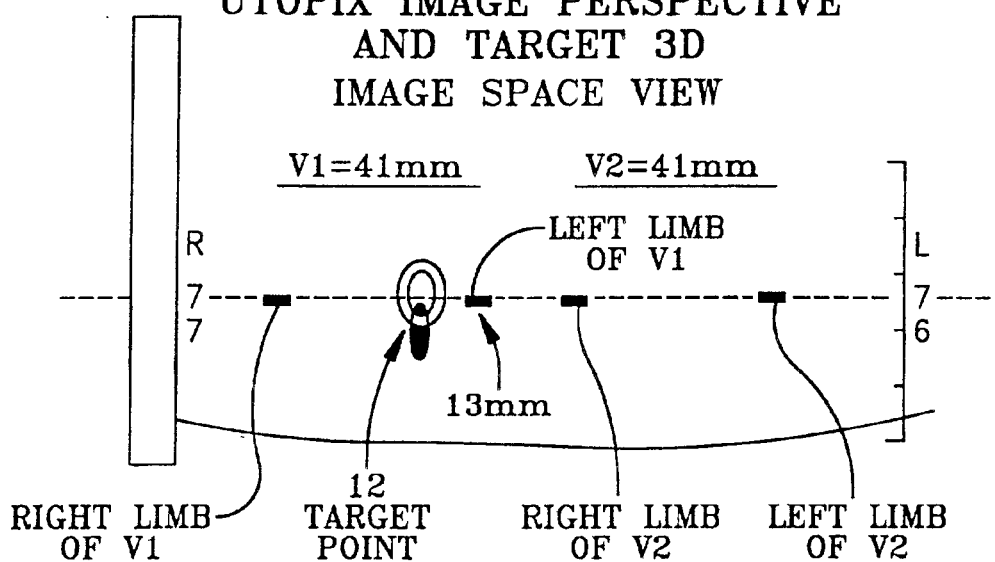
FIG. 10 shows a photograph of an example of real-space cross-sectional image as defined by a device of the present invention, with the corresponding device-generated pattern in the image, to illustrate the operation of a device in accordance with one embodiment of the present invention.
Figure 11:
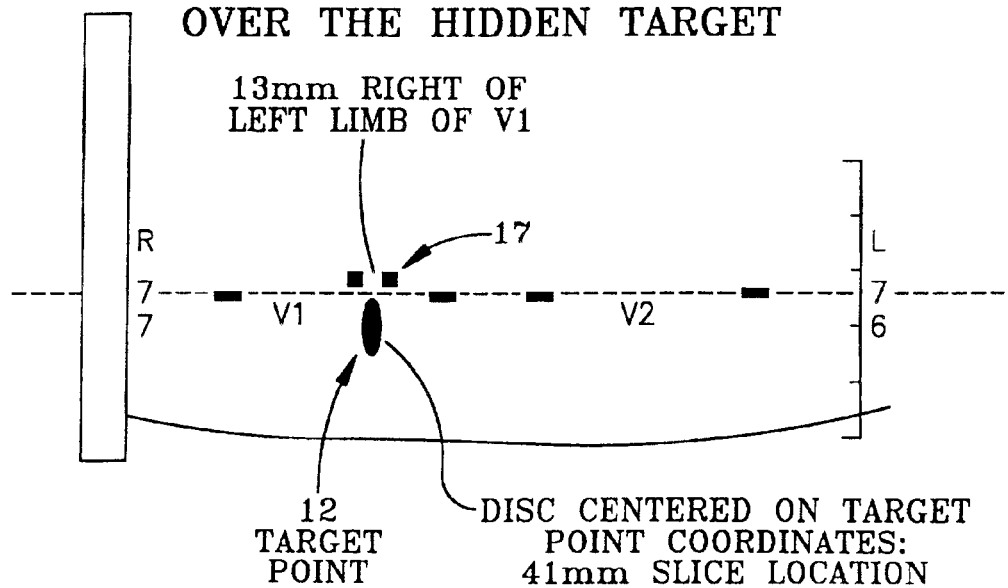
FIG. 11 shows a photograph of an example of real-space cross-sectional image as defined by a device of the present invention, with the corresponding device-generated pattern in the image, to illustrate the operation of a device in accordance with one embodiment of the present invention.
Figure 13:
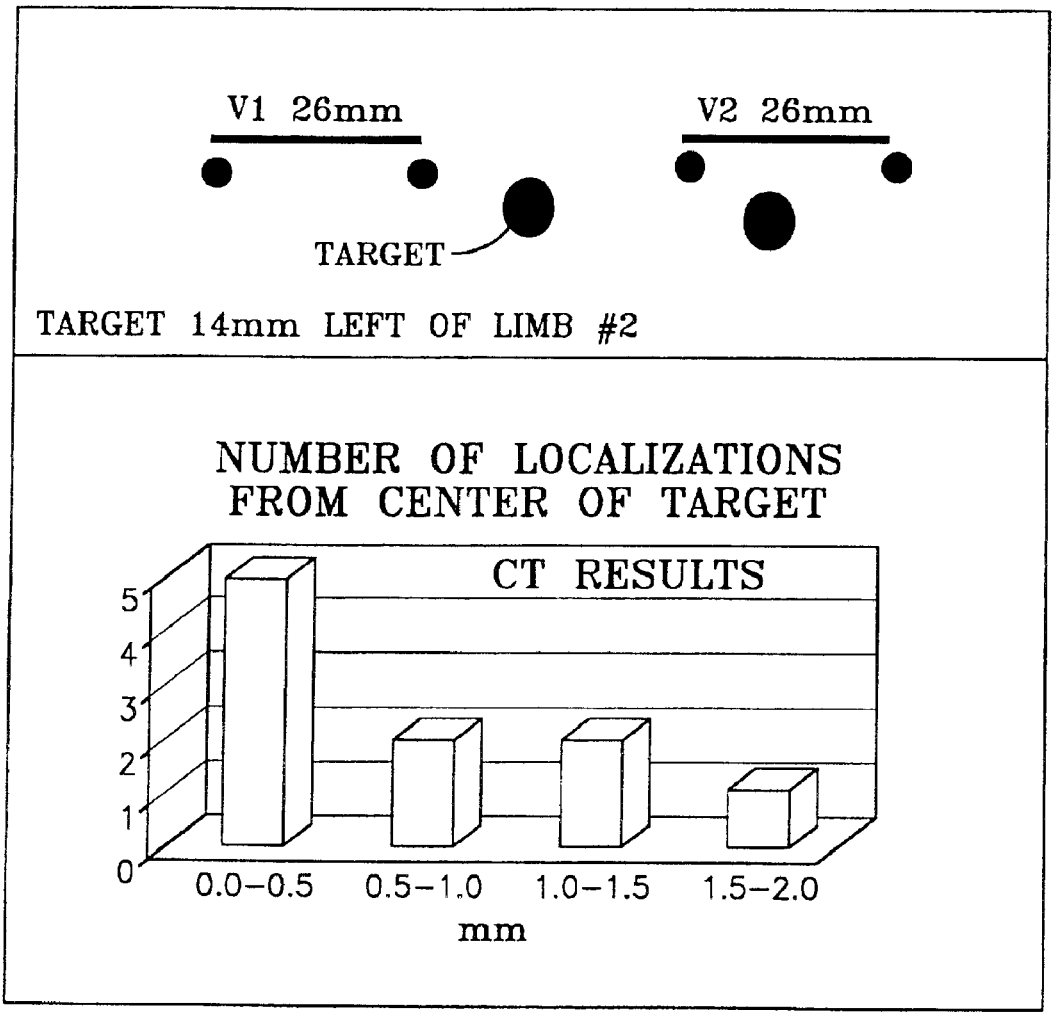
FIG. 13 shows an image perspective view and graph showing the actual results of 10 point localizations with CT using a device of one embodiment of the present invention.

In accordance with the foregoing summary of the invention, the following is a detailed description of a preferred embodiment of the invention, and is presently considered to be the best mode of the invention as applied.

The device of the present invention may be made of any combination of appropriate materials such as sterile, biocompatible materials (e.g., plastic, wire, tubes, catheters, diaphragms, etc.).

As described in more detail below, the device of the present invention has three main components:

1. A lower template portion that aligns to the image plane, and is directly attached to the target tissue, such as a patient's skin or other surface. This component preferably has two "V" patterns with associated mm scale patterns. It also may have a rotation correction scale (V1–V2) printed on it. One of the "V" patterns may be removed to make the template smaller. This component defines the point at which the probe (i.e., instrument, light beam, etc.) enters the tissue. This component may also help the operator keep track of the position of the tissue or patient with respect to the imaging field. It may be directly attached to the patient, and is preferably very thin, typically about 3 mm maximum.

2. A lower frame portion, such as an adhesive attached structure that supports the upper frame portion and helps align the upper frame portion to the lower template portion. This component may have an adhesive clear base, and may be molded to the patient's surface. For instance, it may be in the form of a circular sponge ring (5 mm thick) that engages the intermediate frame portion attached to the upper frame portion or other attachments such as a table. The upper frame portion may be turned in the lower frame portion allowing the operator to bring the upper frame portion parallel to the image plane. This component is placed in a location between the upper frame portion and the lower template portion so that the chosen vector will be correct. In an alternative embodiment the lower template portion may be integrated with the lower frame portion section plane.

3. An upper frame portion that supports/aligns the upper end of the probe (i.e., instrument, light beam, matter beam, etc.) away from the skin. For instance, in the case of a needle, it may be advanced into the device and held by it. In a preferred embodiment, the needle may also be removed from the device allowing for the upper component to be completely removed. The needle could be taken out the upper component and the upper component could be left in place. This is possible since the device in a preferred embodiment is open on one side. The upper component has two "V" patterns. These are used to orient the operator, to confirm the relationship to the image plane as well as confirm the location of the needle or probe.

In a preferred embodiment there are 5 parts as described in the drawings. The intermediate base is a clear plastic cylinder that is attached to the upper frame portion so as to support the "V" patterns with a slot. The upper frame portion has at least one (e.g., two) "V" pattern and supports the optional orthogonal motion small "V" that actually supports the probe. This part slides back and forth in the base part. The third part is a small "V" that has a central slit structure that holds the needle in place, but allows the needle to be removed. This "V" also acts to confirm the location of the probe and moves orthogonal to the large "V" support, allowing for full manipulation of the probe to any chosen vector. In one of the described embodiments, this component slides forwards and backwards orthogonally between the two large "V"'s.

The fourth part is the optional cable-catheter mechanism that moves the large double "V" pattern part horizontally.

The fifth part is the optional cable-catheter mechanism that moves the small "V" pattern orthogonal to the large double "V" pattern.

A sixth part is an optional handle that can be manually moved or moved with a computer remote control mechanical system to adjust the component from a distance the exact required dimensions. This part may be provided with mm dimensions on it guiding the operator.

There are preferably two controls on the handle, one for each orthogonal motion. There may also be an optional control to control the rotation of the upper frame portion with respect to the lower frame portion.

Figure 14:
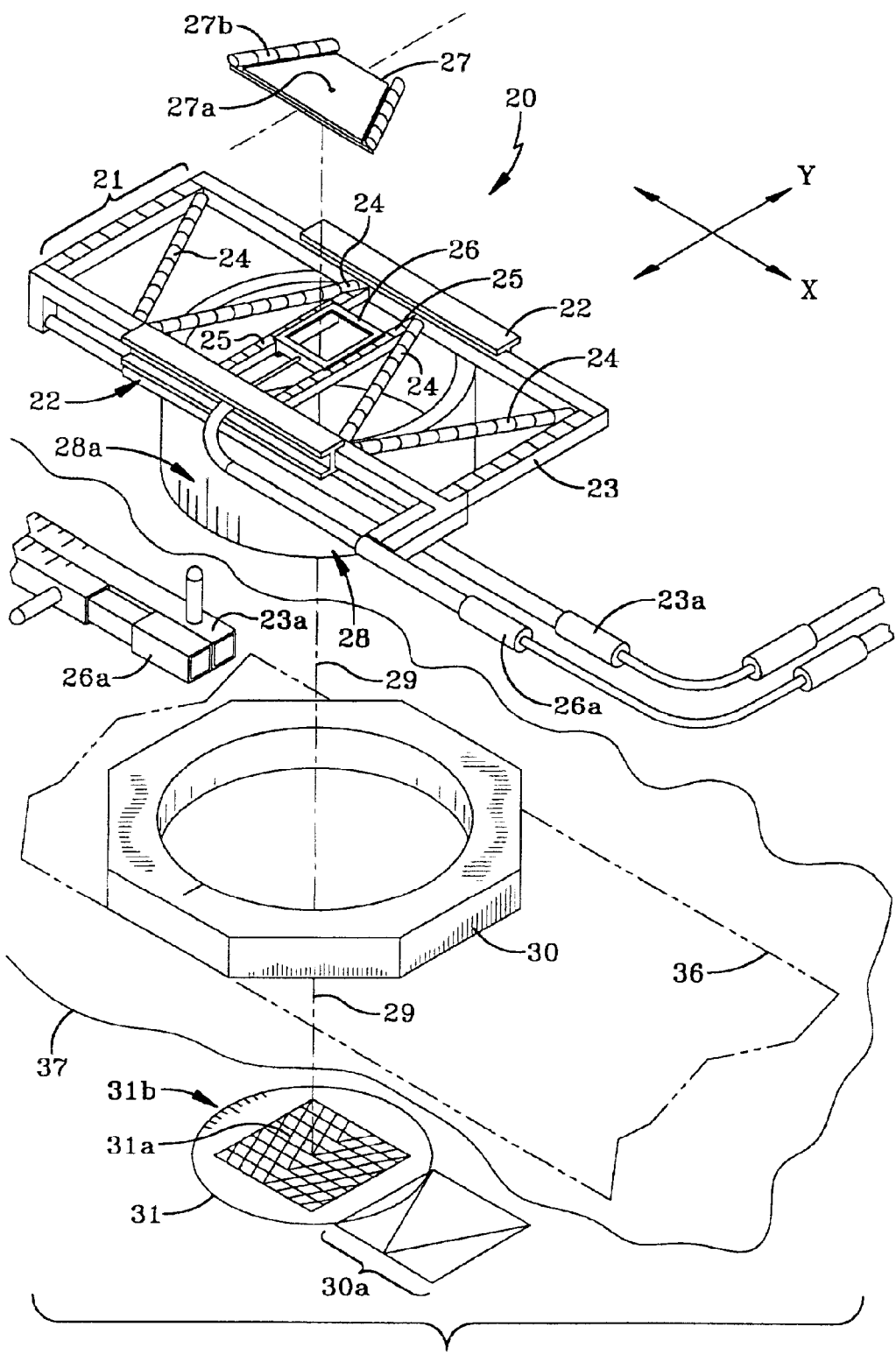
FIG. 14 is an exploded perspective view of a device in accordance with one embodiment of the present invention.

FIG. 14 shows an exploded view of a stereotactic device 20 in accordance with one embodiment of the present invention.

FIG. 14 shows the upper plane of the device defined by an upper frame portion 22 that defines an upper plane 21 and supports a moveable portion 23 that is capable of moving in the X direction by action of actuator 23a. Moveable portion 23 in turn supports the image-conspicuous members 24 that define two 53-degree V's that act as described above to arrange the device to be parallel to the image plane. The moveable portion 23 also includes vertical frame portions 25 that in turn support the moveable portion 26 that is capable of moving in the Y direction by action of actuator 26a. Both actuators 23a and 26a preferably are provided with graduations accordingly with the scale provided on the device respectively representing the distances along the X and Y directions that the alignment aperture must be moved to align it with the target once its position is determined from the imaging device.

The moveable portion 26 may also optionally support either an aperture-bearing material (such as within the square frame of moveable portion 26; not shown), or an aperture-bearing member 27 (having an alignment aperture 27a) that features a 53-degree V-shaped image conspicuous portion 27b that may also be used to align the device. In this embodiment, the aperture-bearing member 27 may be attached atop the moveable portion 26.

Actuators 23a and 26a move the upper frame portions so as to move the alignment aperture over the target vector as seen on the imaging device output. This may be done remotely through the use of a long cable such as a flexible plastic tube that conducts a flexible plastic rod actuator to transmit force. One controls the horizontal motion, and the other controls the vertical motion. The outer tube of each actuator handle is stationary. Naturally, this function may also be carried out at the site of the device with any equivalent actuator.

The principal function of the upper frame portion is to support the V-shaped image conspicuous portion, and to provide a moveable alignment aperture that allows an instrument, stream of matter or beam to be aligned along the determined vector 29 or its adjusted equivalent. Accordingly, the upper frame portion may be made of any clear material appropriate to the imaging application to which it is to be applied. Examples include plastics such as PVC, Mylar, and other non-conductive materials.

The upper frame portion 22 is attached to an intermediate frame portion 28, which in this embodiment is in the form of a cylindrical section. This portion may be supplied with graduations 28a to indicate the degree to which the upper frame portion is out of alignment with the image plane as described above. It is preferred that the intermediate frame portion 28 be a transparent cylindrical plastic tube section that allows the operator to see as much of the target area from as many angles as possible. The function of the intermediate frame portion 28 is to provide separation between the upper frame portion and the lower frame portion. Accordingly, any one or more pieces of various alternative geometries, such as nested sections, or a series of rods in a circular array may also provide this portion.

The intermediate frame portion 28 engages lower frame portion 30, that optionally includes a reference point 30a that can be the reference point for the graduations 28a, to assist the operator in reorienting the upper frame portions to the image plane. The lower frame portion 30 in this embodiment may be a plastic piece that is shaped to engage the intermediate frame portion 28 so as to allow it to rotate with respect to the lower frame portion 30. This portion optionally may be a flexible foam member with a releasable adhesive on its underside adapted to adhere to the target area tissue.

The lower frame portion 30 defines the lower plane 30a upon resting on the target tissue, and may optionally comprise a targeting template either integral with the lower frame portion 30 (not shown) or provided as a separate lower template piece 31 (which may also ultimately define the lower plane 30a). The device may have a fixative, such as an adhesive, to hold it in place against the tissue or body. The device may also have optional attachment strap 36 (shown in phantom) that may be attached to the lower frame portion 30, for instance, and that may be elastic, nylon, or any other appropriate material, affixed using an appropriate means such as a hook-and-loop closure, buckles, buttons, etc. The device may also have attached to it a sterile drape 37 (shown in a partially sectioned view). The sterile drape 37 may be attached to the optional attachment strap 36, or directly to other portions of the device where an attachment strap is not used.

The separate lower template piece 31 has a dual 53-degree V design allowing it to be aligned with the image plane. In the displayed embodiment, the separate lower template piece 31 has a principal template V figure. 31a centered below the center reference point of the alignment aperture 27a. This principal template allows the operator to assess the position to which the alignment aperture 27a must be moved to form a vector directed to the target, as described herein. The separate lower template piece 31 may be provided with a series of V-shaped patterns that represent unit distances from the main V limb in the lower template. This scale can be used with the similar scale accompanying one of the Vs in the upper frame portion, so that where the target is seen using the imaging device, the operator may determine points of entry through the upper and lower planes to establish a vector to the target.

The separate lower template piece 31 may be provided with graduations 31b, if desired, to assist in aligning the template to the image plane.

The separate lower template piece 31 may itself optionally have a releasable adhesive on its underside adapted to adhere to the target area tissue. It may also have a perforation (not shown) between its principal and secondary V design to allow the latter to be separated from the former following alignment with the image plane. The separate piece 31 in this embodiment may be made of a transparent plastic such as Mylar.

The lower frame portion may also be provided with an attached sterile drape (not shown) that may be used to protect the target area from contamination. This may be attached through adhesives, stitching, or any other means for attaching material to a relatively rigid part.

Figure 15:
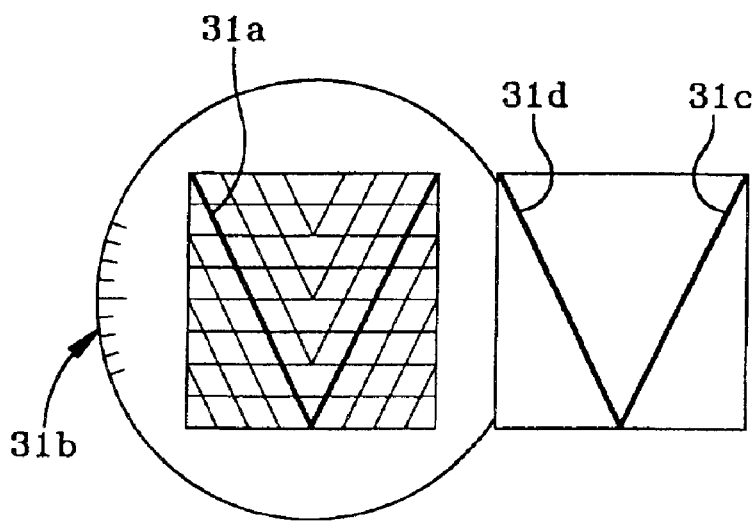
FIG. 15 is a plan view of a lower template portion of a device in accordance with one embodiment of the present invention.

The separate piece 31 is also shown in FIG. 15. This separate template piece may be used for a CT imager, and may be made with image conspicuous materials, such as image conspicuous inks or paints that may be printed or silk-screened upon the surface, or that may be formed into the article itself (such as a piece of metal molded into a plastic piece). The pattern on the separate piece 31 preferably has a principal V design 31a and a secondary principal V design 31c. This device may also have a perforation along perforation line 31d to allow the secondary principal V design 31c to be separated from the principal V design 31a.

Figure 16:
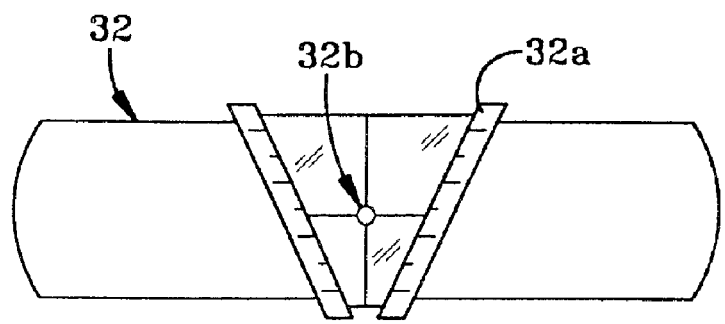
FIG. 16 is a plan view of an alternative lower template portion of a device in accordance with another embodiment of the present invention.

An alternative separate piece, shown in FIG. 16, for use as the lower template may be an adhesive bandage-style strip 32 bearing image conspicuous members forming a 53-degree V figure with optional rulings 32a showing the distance from the base of the V (as described above), with targeting cross-hairs and a target aperture 32b. This type of template is appropriate for MRI use where the tubular members are filled with an image conspicuous material.

Figure 17:
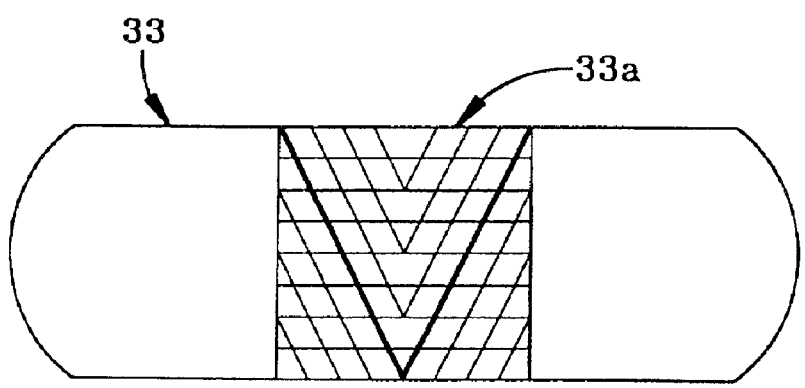
FIG. 17 is a plan view of an alternative lower template portion of a device in accordance with another embodiment of the present invention.

Another alternative separate piece for use as the lower template is shown in FIG. 17, and may be an adhesive bandage-style strip 33 bearing an image conspicuous pattern forming a 53-degree V figure with optional rulings 33a showing the distance from the base of the V (as described above). This type of template may be printed with image conspicuous material similar to that shown in FIG. 15.

Figure 18:
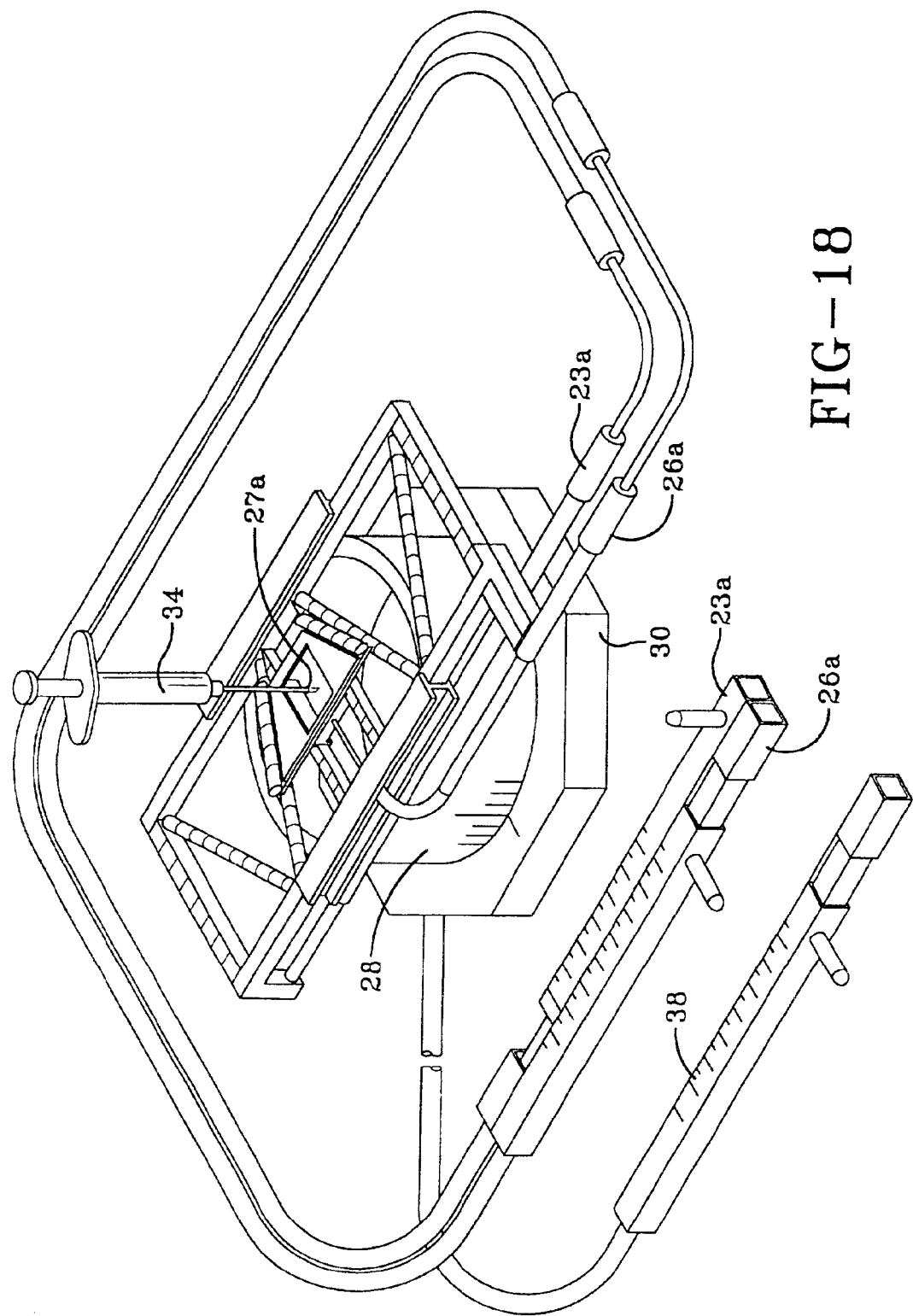
FIG. 18 is a perspective view of a device in accordance with one embodiment of the present invention.

FIG. 18 shows the device shown in FIG. 14 (without item 31, the attachment strap and the sterile drape) in an assembled configuration. FIG. 18 shows an instrument such as a syringe 34, placed through alignment aperture 27a. FIG. 18 also shows intermediate frame portion 28 fitted into lower frame portion 30. Actuators 23a and 26a move the upper frame portions so as to move the alignment aperture over the target vector as seen on the imaging device output.

FIG. 18 also shows an optional additional actuator 38 that is mounted onto lower portion 30 and is attached so as to allow the intermediate frame portion 28 to be rotated with respect to the lower portion 30, and works in the same way as actuators 23a and 26a, except that the stationary outer sleeve of the actuator is attached to the lower portion 30 while the moveable inner core is attached to the frame 28. This allows remote alignment of the upper plane portion with the image plane. The actuator 38 may also be provided with graduations indicating the required distance of rotation to bring the device parallel to the image plane, such as may accord with the reading obtained from graduations 28a.

Figure 19:
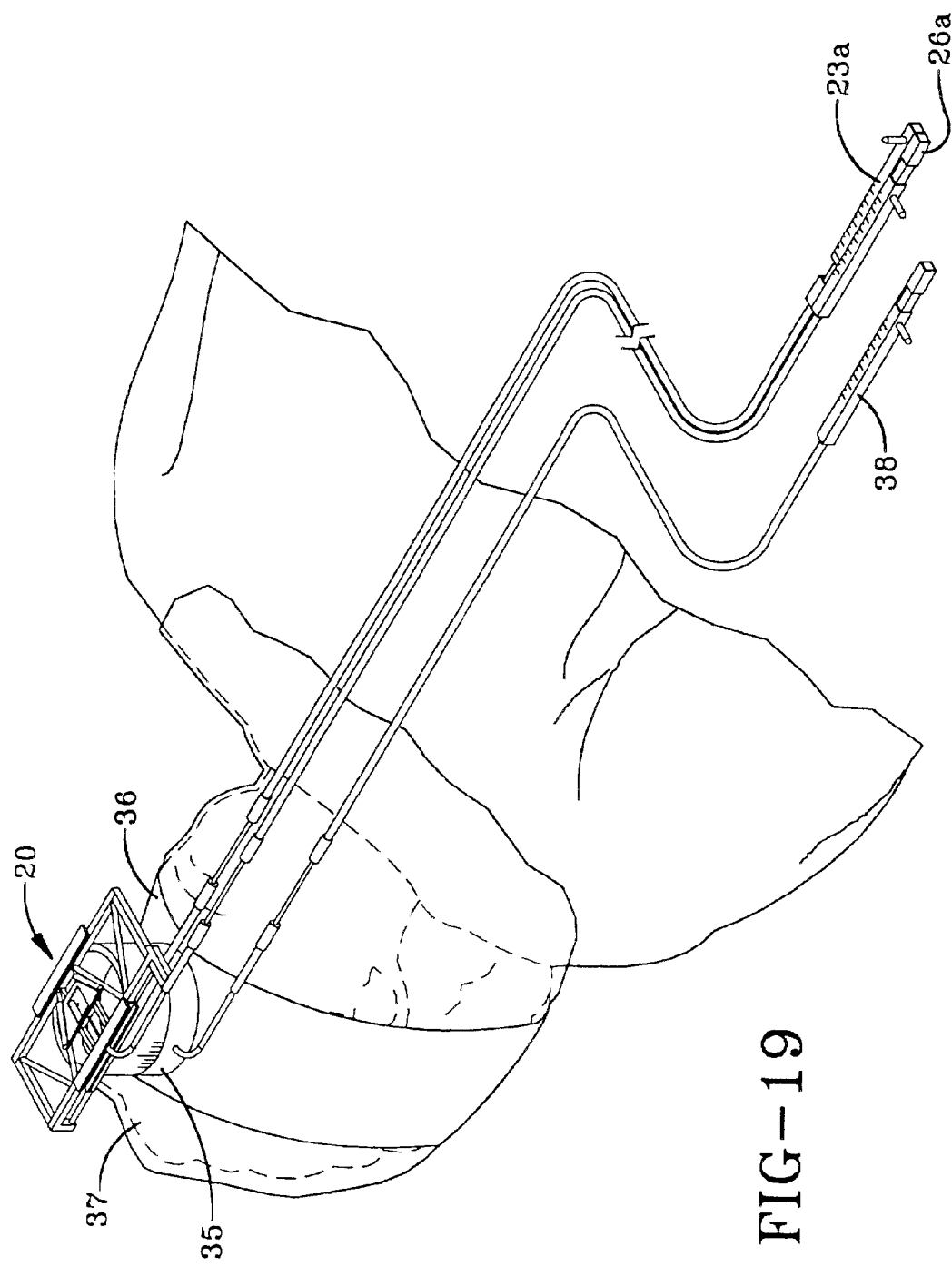
FIG. 19 is a perspective view of a device in accordance with one embodiment of the present invention, placed on a patient.

FIG. 19 shows an alternative lower portion and attachment variation in the stereotactic device 20 (shown attached to the head of a patient), otherwise the same as that shown in FIGS. 14 and 18. FIG. 19 shows lower frame portion 35 (a mating piece of cylindrical plastic) in place of lower portion 30 shown in FIGS. 14 and 18. Lower frame portion 35 as shown may be attached to a device such as an elastic band 36 to hold the device 20 in place (with frame portion 28, and the balance of the device as shown in FIGS. 14 and 18). This may be done through use of appropriate adhesives, or stitching the elastic onto the lower frame portion 35 through holes provided along its bottom (not shown). An aperture is provided in the elastic band or other attachment means, to permit access to the target area through it. Preferably, the elastic band is in turn attached to a sterile drape 37 that may be used to protect the target area from contamination.

An alternative remote control actuator 50 (which is a double actuator similar to the 23a/26a actuator described above) is shown in FIGS. 20a and 20b. This type of actuator features an outer sleeve such as 51, and an inner screw 52. The outer sleeve 52 has an engagement structure such as extension 53 that engages the threads of screw member 52. The extension member 53 also has the property that its engagement with the threads of screw member 52 may be overcome by direct linear movement. This will normally be brought about through the use of loose tolerances in the engagement, or through the screw or extension member or both being of sufficiently flexible material to allow the threading engagement to be overcome, and the screw and sleeve moved directly with respect to one another. As an alternative to the structure shown in FIGS. 20a and 20b, the extension member may extend directly into the hollow sleeve from one of its interior surfaces.

In a preferred embodiment, the threads of the inner screw are preferably chosen so as to accord with a given distance measurement (such as 1 mm distance between threads), and so each turn of the inner screw accords with a respective partial distance measurement, e.g., one half turn equals ½ mm distance.

This actuator allows the operator to sense a tactile and/or audible feedback with the direct movement of the inner screw within the outer sleeve when movement of the upper alignment portion is needed; and to easily move the actuator a fraction of the distance measurement for refinement of position by turning the inner screw 1/nth of a turn to approximate an additional fractional distance measurement.

It will be appreciated that the optional remote control actuator(s) used in accordance with the present invention may be any alternative actuating means, such as hydraulic or servo actuated, etc.

Figure 20:
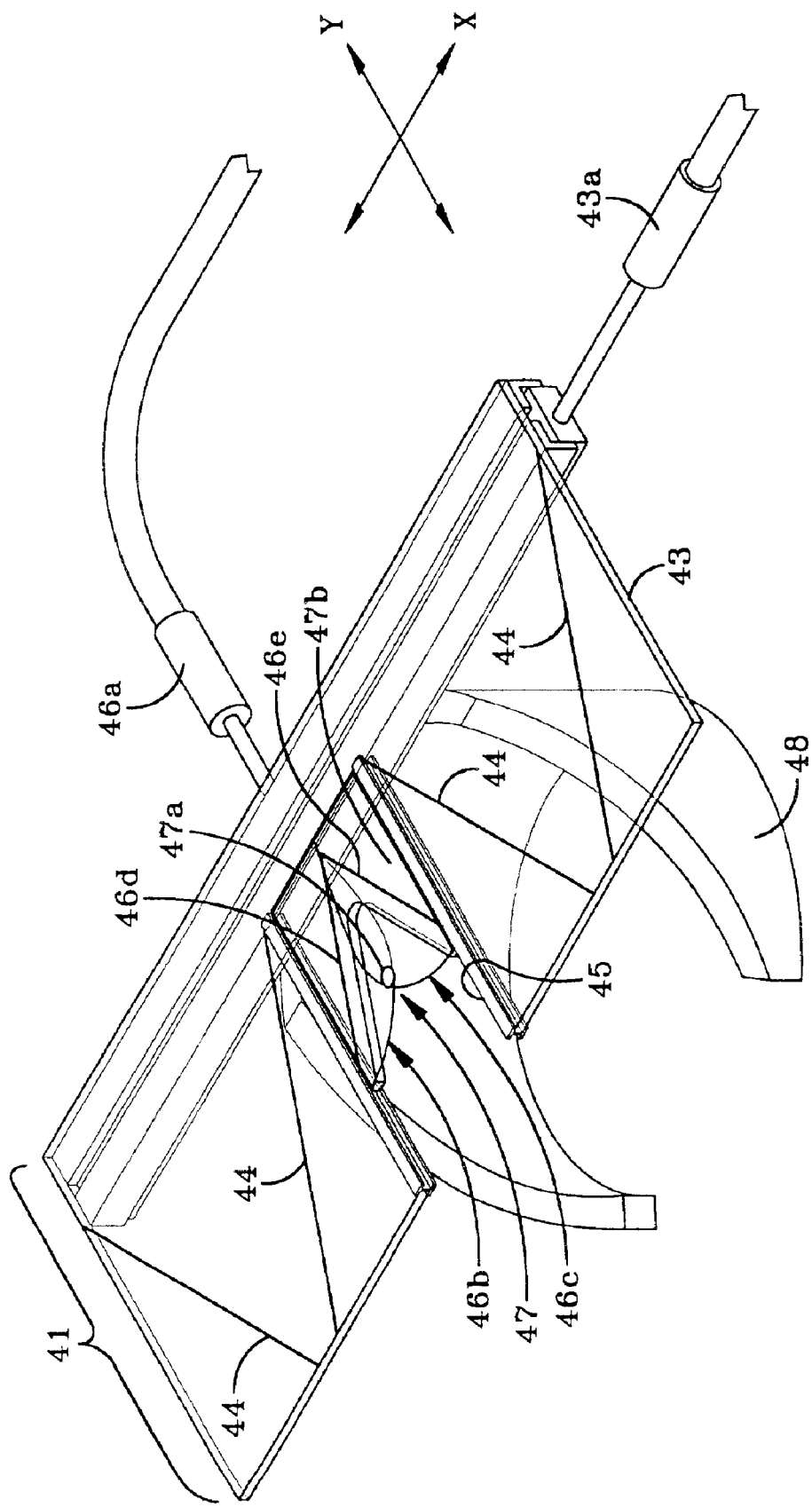
FIG. 20 is a perspective view of a device in accordance with another embodiment of the present invention.

FIG. 20 shows an alternative architecture for the upper and intermediate frame portions of the device shown in FIGS. 14 and 18. This device portion may be used with any of the above-described features not inconsistent with its function described below.

FIG. 20 shows the upper plane 41 of the device defined by an upper frame portion 42 that supports a moveable portion 43 that is capable of moving in the X direction by action of actuator 43a (that uses the same tubular type plunger actuator). Moveable portion 43 in turn supports the image-conspicuous members 44 that define two 53-degree Vs (i.e., formed from wires imbedded in or otherwise held within or adhered to a plastic planar member; i.e. for use with a CT imager) that act as described above to arrange the device to be parallel to the image plane. The moveable portion 43 also includes vertical frame portions 45 that in turn support the moveable portion 46 that is capable of moving in the Y direction by action of actuator 46a. In this embodiment, the moveable portion 46 is made up of two flexible plastic pieces 46b and 46c that cooperate to form an aperture-bearing member 47 (having an alignment aperture 47a) that may also feature a 53-degree V-shaped image conspicuous portion 47b that may also be used to align the device. The flexible plastic pieces allow the needle or probe to be pushed through the device without changing the vector.

The two flexible plastic pieces 46b and 46c are sufficiently flexible to allow the needle device to be moved laterally (i.e., along vector Y) with respect to an instrument once placed through the alignment aperture 47a. The flexible plastic pieces 46b and 46c may also be provided with image-conspicuous members 46d and 46e, respectively, similar to image-conspicuous members 44 to define another "V" pattern for alignment purposes.

The intermediate frame portion 48 also may be provided with an opening in the same direction to allow the device to be moved laterally. This design permits the device to be moved from around an instrument once the instrument is placed into the target. This feature is particularly useful in applications where an instrument is placed in soft tissue of a patient where it would be disadvantageous to maintain the instrument immobilized (i.e., in the alignment aperture) once placed into the target tissue while the patient is breathing. This feature generally allows the operator to remove the device from the patient once the instrument has been placed in the target for greater visibility and mobility.

Actuators 43a and 46a move the upper frame portions so as to move the alignment aperture over the target vector as seen on the imaging device output. This may be done remotely through the use of a long cable such as a flexible plastic tube that conducts a flexible plastic rod actuator to transmit force in the manner of a cable-catheter mechanism. Naturally, this function may also be carried out at the site of the device with any equivalent actuator or manual movement.

In order to operate the device of the present invention, the following steps preferably may be followed:
1. The patient is imaged and the target is found.
2. A non-sterile pattern similar to or identical to the base component is placed on the skin approximately at the entry point.

3. Another image is acquired.
4. The relationship of the image plane to the pattern is measured.
5. If the pattern is not parallel then it is rotated based on the rotation correction scale.
6. Another image is made to confirm the pattern is parallel.
7. If parallel, then the entry point is found by drawing a vector on the computer screen.
8. The entry point location may be localized on the pattern and the skin may be marked (ink) at that point.
9. The skin preferably is prepared for sterile handling and treatment.
10. A sterile lower pattern is placed over the entry point parallel to the section plane. This is done by measuring the V1 and V2 image plane intersection distances to confirm that they are the same.
11. The needle is pushed through the sterile base pattern at the desired entry specific point (for example where the distance on the pattern measures (14 mm)) and is then removed.
12. The skin may be numbed to anesthetize at the chosen point of entry.
13. The upper and intermediate frame portions are attached to the patient so that the chosen vector will be correct for the target, the entry point, and the upper component's range of motion, the needle is placed in the upper support.
14. The upper frame portion/intermediate frame portion combination is then placed in the corresponding lower frame portion ring and is oriented parallel to the image plane.
15. An image is acquired to confirm that everything is aligned.
16. The vector is drawn on the image through the needle entry point.
17. The upper component is then moved to correct dimensions to confirm that the needle is pointing at the target, by remote control.
18. The needle is then confirmed to be in the correct vector position outside the patient and the distance to the target is measured.
19. The needle may then be pushed to the target using local anesthetic.
20. The needle position in the target may then be confirmed by imaging (where the FIG. 20 embodiment is used, the open architecture allows the operator to remove the upper plane portion and supporting frame once the target has been reached, allowing the operator to proceed with the procedure unobstructed by the device).
21. The upper component can be removed.
22. The procedure is completed, such as through administration of medication or removing tissue for biopsy.
23. The needle is removed or the rest of the components are removed as desired.

Figure 21:
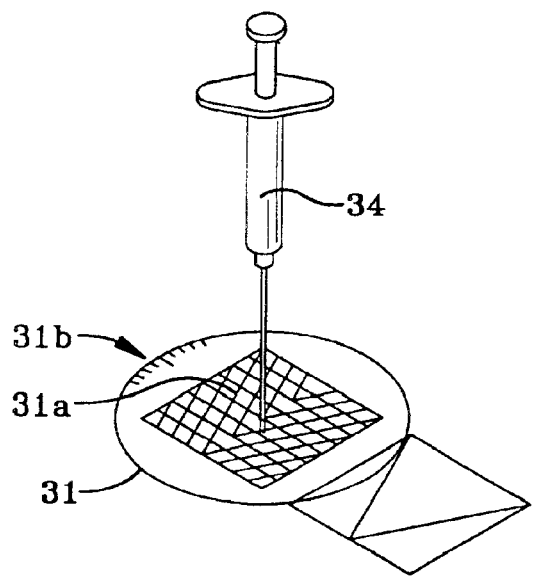
FIG. 21 is a photograph view illustrating a step in the operation of a device in accordance with one embodiment of the present invention.

In FIG. 21, the target point for entry is found and the probe is placed at a standard position through the lower template pattern 31. In this case it is at the 24-mm line.

Figure 22:
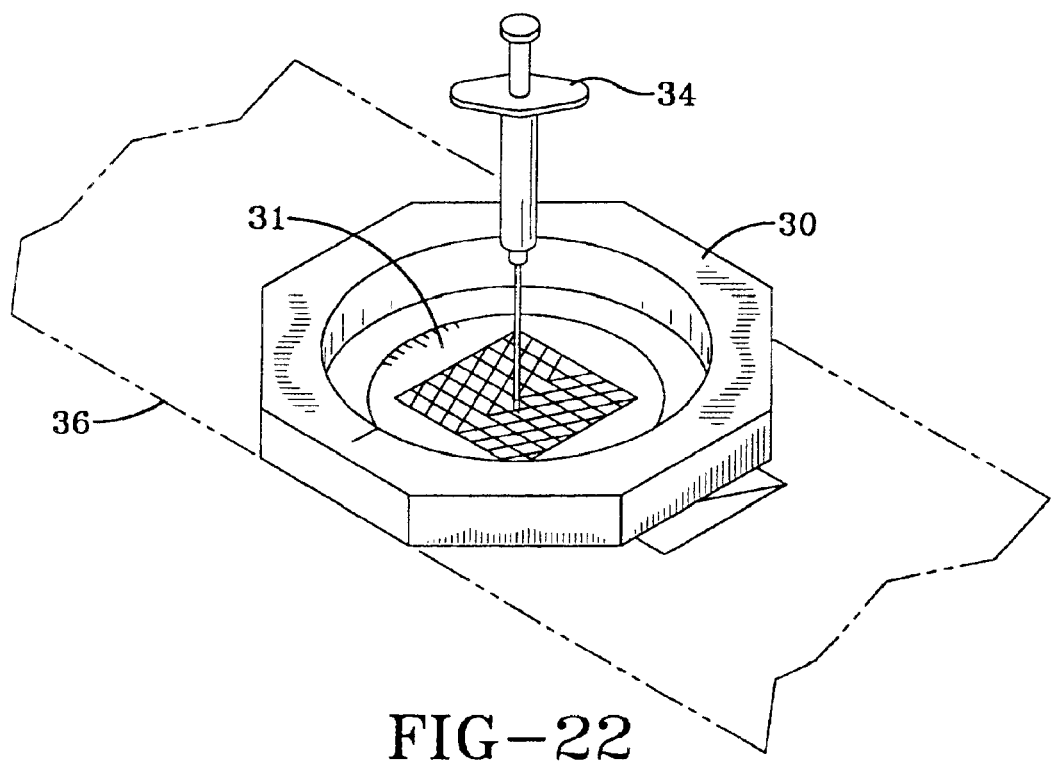
FIG. 22 is a photograph view illustrating a step in the operation of a device in accordance with one embodiment of the present invention.

In FIG. 22, the lower frame portion 30 is then placed in the correct location to support the intermediate and upper frame portions 28 and 22.

Figure 23:
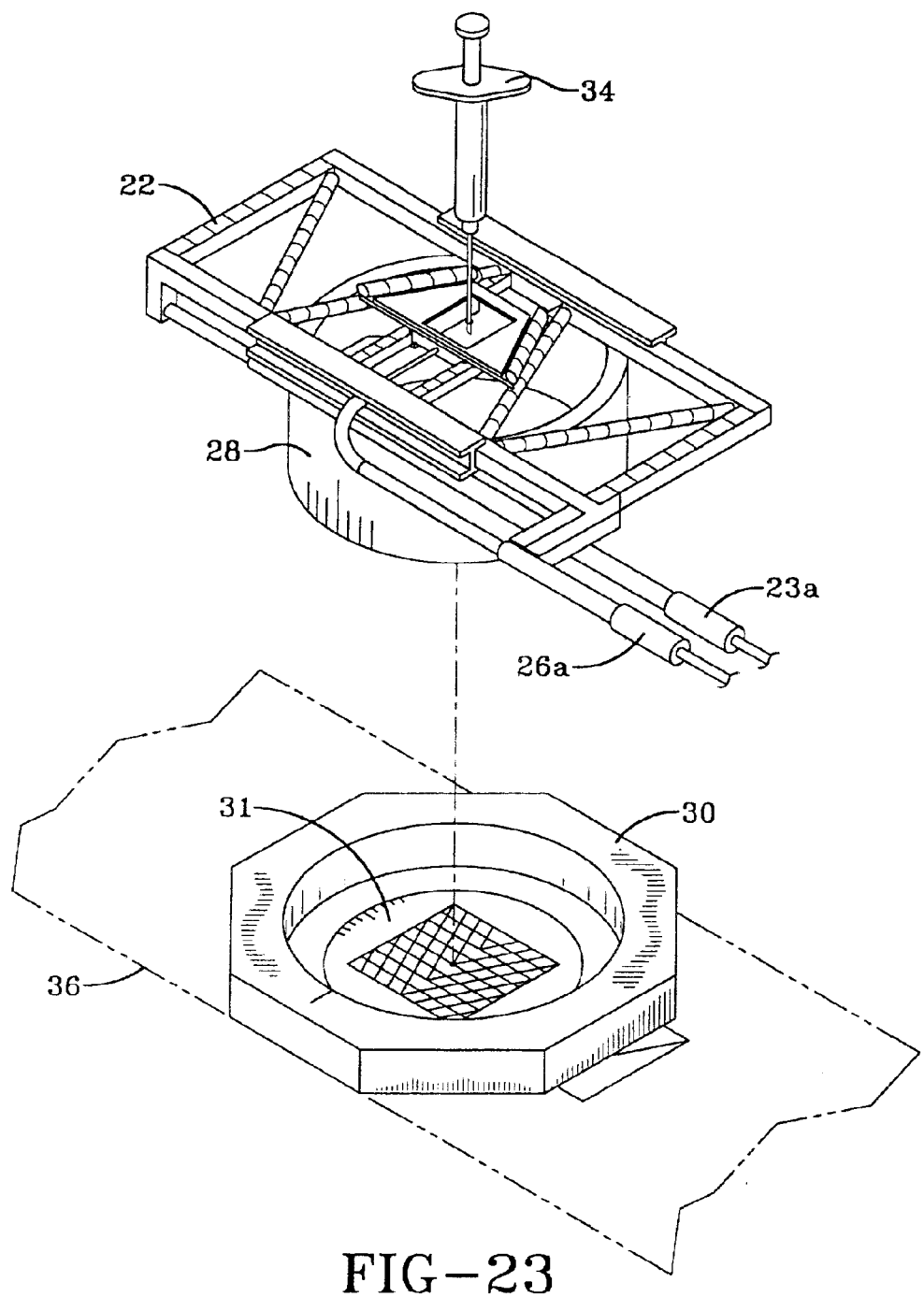
FIG. 23 is a photograph view illustrating a step in the operation of a device in accordance with one embodiment of the present invention.

In FIG. 23, the upper and intermediate frame portions 22 and 28 are put in the lower frame portion 30. This may be done either by sliding the device over the needle through an open slot in the device as provided in the embodiment of FIG. 20, or by temporarily removing the needle, and replacing the needle through the alignment aperture 27a in the embodiment of FIGS. 14 and 18. The upper frame portion may then be manipulated by remote control to the correct vector, and then the needle is pushed to toward the target.

Figure 24:
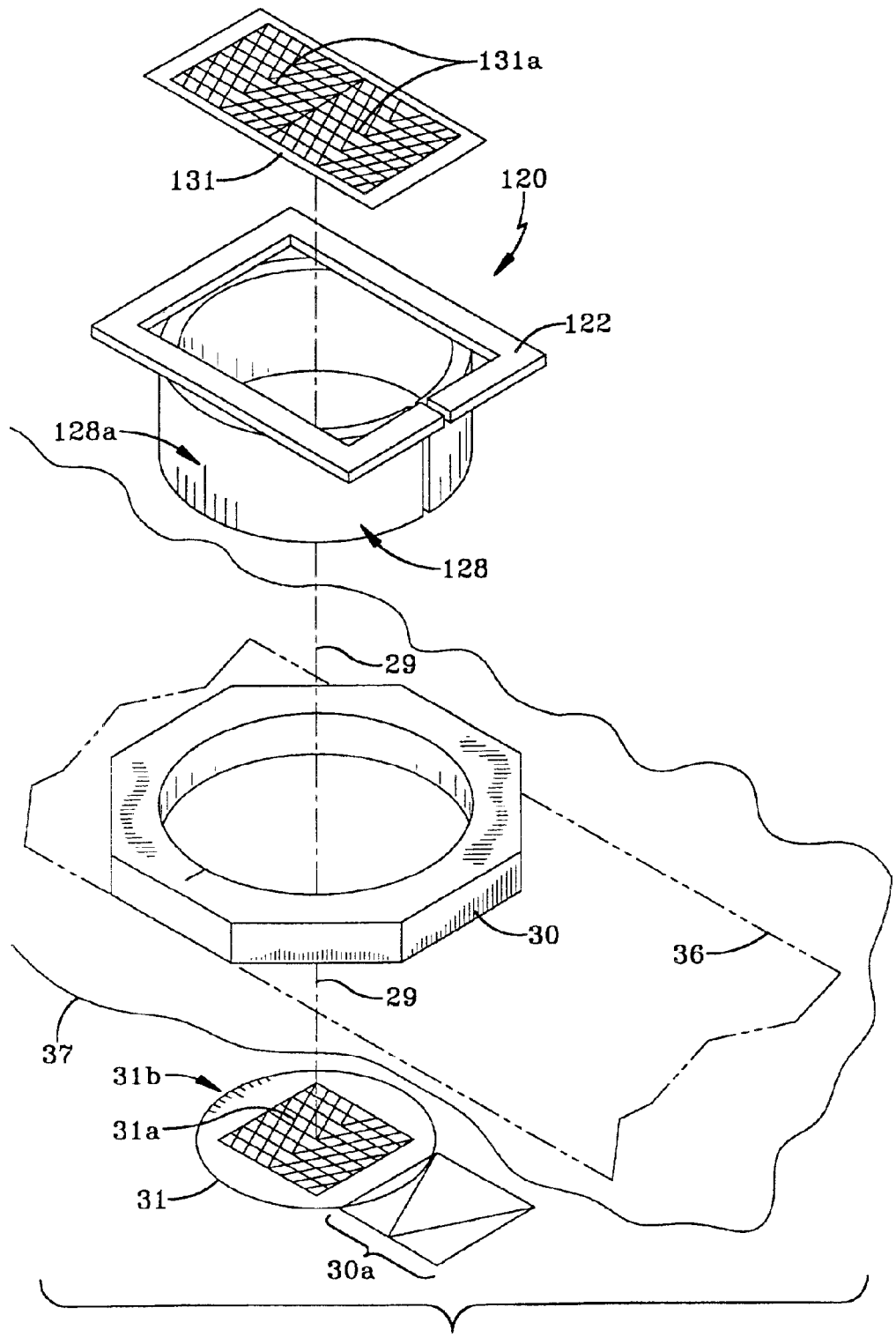
FIG. 24 is a perspective view of an alternative remote actuator that may be used in accordance with another embodiment of the present invention.

FIG. 24 shows an exploded view of a stereotactic device 120 in accordance with one embodiment of the present invention.

FIG. 14 shows the upper plane of the device defined by an upper frame portion 122 that defines an upper plane containing an upper template piece 131 with a dual 53-degree V design 131a allowing it to be aligned with the image plane as described above.

The principal function of the upper frame portion is to support the upper template piece, which is preferably perforable or transparent to allow an instrument, stream of matter or beam to be inserted or passed through and aligned along the determined vector. Accordingly, the upper frame portion may be made of any clear material appropriate to the imaging application to which it is to be applied. Examples include plastics such as PVC, Mylar, and other non-conductive materials.

The upper frame portion 122 is attached to an intermediate frame portion 128, which in this embodiment is in the form of a cylindrical section. This portion may be supplied with graduations 128a to indicate the degree to which the upper frame portion is out of alignment with the image plane as described above. It is preferred that the intermediate frame portion 128 be a transparent cylindrical plastic tube section that allows the operator to see as much of the target area from as many angles as possible. The function of the intermediate frame portion 128 is to provide separation between the upper frame portion and the lower frame portion. Accordingly, any one or more pieces of various alternative geometries, such as nested sections, or a series of rods in a circular array may also provide this portion.

The intermediate frame portion 128 engages lower frame portion 130, that optionally includes a reference point 130a that can be the reference point for the graduations 128a, to assist the operator in reorienting the upper frame portions to the image plane. The lower frame portion 130 in this embodiment may be a plastic piece that is shaped to engage the intermediate frame portion 128 so as to allow it to rotate with respect to the lower frame portion 130. This portion optionally may be a flexible foam member with a releasable adhesive on its underside adapted to adhere to the target area tissue.

The intermediate frame portion 128 and upper frame portion 122 may be provided with an opening to allow the device to be moved laterally. This design permits the device to be moved from around an instrument once the instrument is placed into the target. This feature is particularly useful in applications where an instrument is placed in soft tissue of a patient where it would be disadvantageous to maintain the instrument immobilized (i.e., in the alignment aperture) once placed into the target tissue while the patient is breathing. This feature generally allows the operator to remove the device from the patient once the instrument has been placed in the target for greater visibility and mobility.

The lower frame portion 30 defines the lower plane upon resting on the target tissue, and may optionally comprise a targeting template either integral with the lower frame portion 30 (not shown) or provided as a separate lower template piece 31 (which may also ultimately define the lower plane). The device may have a fixative, such as an adhesive, to hold it in place against the tissue or body. The device may also have optional attachment strap 36 (shown in phantom) that may be attached to the lower frame portion 30, for instance, and that may be elastic, nylon, or any other appropriate material, affixed using an appropriate means such as a hook-and-loop closure, buckles, buttons, etc. The device may also have attached to it a sterile drape 37 (shown in a partially sectioned view). The sterile drape 37 may be attached to the optional attachment strap 36, or directly to other portions of the device where an attachment strap is not used.

The separate lower template piece 31 has a dual 53-degree V design allowing it to be aligned with the image plane. In the displayed embodiment, the separate lower template piece 31 has a principal template V FIG. 31a centered below the center reference point of the upper template piece. The separate lower template piece 31 may be provided with a series of V-shaped patterns that represent unit distances from the main V limb in the lower template. This scale can be used with the similar scale accompanying one of the Vs in the upper frame portion, so that where the target is seen using the imaging device, the operation may determine points of entry through the upper and lower planes to establish a vector to the target.

The separate lower template piece 31 may be provided with graduations 31b, if desired, to assist in aligning the template to the image plane.

The separate lower template piece 31 may itself optionally have a releasable adhesive on its underside adapted to adhere to the target area tissue. It may also have a perforation (not shown) between its principal and secondary V design to allow the latter to be separated from the former following alignment with the image plane. The separate piece 31 in this embodiment may be made of a transparent plastic such as Mylar.

Figure 27:
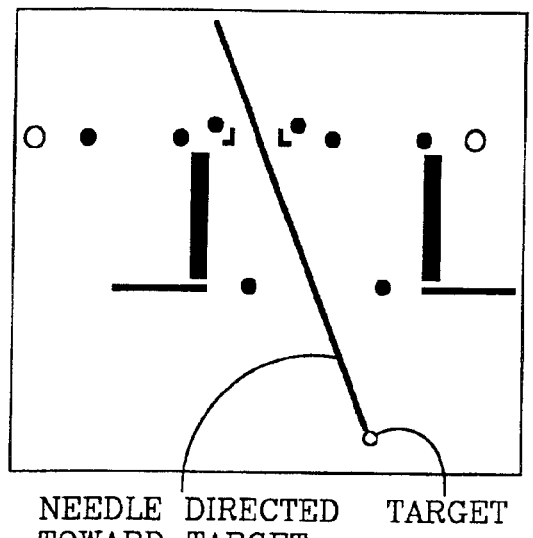
FIG. 27 is a photograph of an image perspective view illustrating a step in the operation of a device in accordance with one embodiment of the present invention.

The lower frame portion may also be provided with an attached sterile drape (not shown) that may be used to protect the target area from contamination. This may be attached through adhesives, stitching, or any other means for attaching material to a relatively rigid part. FIGS. 25–27 show the stepwise use of a device in accordance with the present invention when used on a live subject in conjunction with an imaging device.

In another example of the device's application, it may be used in conjunction with a fluoroscope. In fluoroscopy, the operator views the tissue and the target in the same fashion as watching a television. The lower plane image is placed over the target, and the end of the probe (i.e., such as a needle) is positioned over the target live in real time. At this point, the skin may be anesthetized. The upper plane portion of the device is then placed over the target site (with the optional drape and support base). The probe is then placed at the target skin entry point and the upper plane portion would be aligned. The other end of the needle is placed in the alignment structure (whether using either the FIG. 18 or 20 embodiment). Another fluoroscopic image is then acquired to find the target. By remote control, the upper supports are manipulated orthogonal drive until the probe is seen as just a dot (the probe at this point being parallel to the target vector).

The fluoroscope can then be adjusted to a different angle and the operator can view the image in real time as the probe is advanced toward the target. Where the FIG. 20 embodiment is used, the open architecture allows the operator to remove the upper plane portion and supporting frame once the target has been reached, allowing the operator to proceed with the procedure unobstructed by the device.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

What is claimed is:

1. A method of placing a probe or defining a vector from outside a tissue into a target area located within said tissue using an imaging device, said target area being within reach of said probe from a targeting surface of said tissue, said method comprising:

(1) establishing a lower plane substantially at said surface of said tissue, said lower plane comprising a lower vector point, and said lower plane portion comprising a lower plane template comprising a pair of angled members of an imager-conspicuous material, each of said pair of angled members defining an angle of about 53 degrees;

(2) establishing an upper plane above said surface of said tissue, said upper plane comprising an upper plane template comprising a pair of adjacent angled members comprising an imager-conspicuous material, said pair of adjacent angled members aligned such that said pair of adjacent angled members open in substantially parallel directions, and wherein said angle defined by each of said pair of adjacent angled members defines an angle of about 53 degrees;

(3) providing an alignment structure comprising an upper vector point adapted to move parallel to said upper plane, so as to be able to define a vector passing through said upper and lower vector points;

(4) if not so aligned, aligning said upper plane and lower plane templates such that said image plane of said imaging device is aligned perpendicular to said bisectors of each of said adjacent angled members;

(5) determining the position of said target area with respect to an entrance point through said lower plane template;

(6) adjusting said alignment structure so as to form a vector containing said entrance point and a point in said target area, and (7) passing said probe along said vector to said target area.

2. A method of placing a probe or defining a vector from outside a tissue into a target area located within said tissue using an imaging device, said target area being within reach of said probe from a targeting surface of said tissue, said method comprising:

(1) establishing a lower plane substantially at said surface of said tissue, said lower plane comprising a perforable material comprising a lower plane template comprising a pair of adjacent angle patterns of an imager-conspicuous material, each of said pair of adjacent angle patterns being aligned such that said adjacent angle patterns open in a substantially parallel direction, and defining an angle of about 53 degrees;

(2) establishing an upper plane above said surface of said tissue, said upper plane comprising a perforable material comprising an upper plane template comprising a pair of adjacent angle patterns comprising an imager-conspicuous material, each of said pair of adjacent angle patterns being aligned such that said adjacent angle patterns open in a substantially parallel direction, and defining an angle of about 53 degrees;

(3) if not so aligned, aligning said upper plane and lower plane templates such that said image plane of said imaging device is aligned perpendicular to said bisectors of each of said adjacent angled members;

(4) determining the position of said target area with respect to vector points through said upper plane template and lower plane template an entrance point through said lower plane template; and (5) passing said probe along a vector through said vector points to said target area.

* * * * *

UNITED STATES PATENT AND TRADEMARK OFFICE
CERTIFICATE OF CORRECTION

PATENT NO. : 6,872,213 B2
DATED : March 29, 2005
INVENTOR(S) : Chakeres

It is certified that error appears in the above-identified patent and that said Letters Patent is hereby corrected as shown below:

Title page,
Item [56], References Cited, please add -- OTHER PUBLICATIONS
1. OREL et al., Staging of Suspected Breast Cancer: Effect of MR Imaging and MR-guided Biopsy, Radiology 1995;196:115-122.
2. STELLING, Breast Cancer Staging with Contrast Material-Enhanced MR Imaging: Should it Change Patient Treatment?, Radiology 1995; 196:16-18.
3. MUMTAZ et al., Laster Therapy for Breast Cancer: MR Imaging and Histophathologic Correclation, Radiology 1996; 200: 651-658.
4. OREL et al., MR Imaging-Guided Localization and Biopsy of Breast Lesions: Initial Experience, Radiology 1994: 193: 97-102. --

Column 8,
Line 66, please delete "V1 and V1" and insert -- V1 and V2 --.

Column 9,
Line 51, please delete "V2 In" and insert -- V2. In --.

Column 16,
Line 26, please delete "figure. 31a" and insert -- figure 31a --.

Column 20,
Line 4, please delete "Fig. 14" and insert -- Fig. 24 --.
Line 7, please delete "131 a" and insert -- 131a --.

Signed and Sealed this

Second Day of August, 2005

JON W. DUDAS
*Director of the United States Patent and Trademark Office*